(12) United States Patent
Reed et al.

(10) Patent No.: US 8,916,168 B2
(45) Date of Patent: Dec. 23, 2014

(54) LEISHMANIA STEROL 24-C-METHYLTRANSFERASE COMPOSITIONS FOR THE PREVENTION, TREATMENT AND DIAGNOSIS OF LEISHMANIASIS

(75) Inventors: Steven Reed, Bellevue, WA (US); Yasuyuki Goto, Seattle, WA (US)

(73) Assignee: Infectious Disease Research Institute, Seattle, WA (US)

( * ) Notice: Subject to any disclaimer, the term of this patent is extended or adjusted under 35 U.S.C. 154(b) by 885 days.

(21) Appl. No.: 12/171,729

(22) Filed: Jul. 11, 2008

(65) Prior Publication Data

US 2009/0041798 A1    Feb. 12, 2009

Related U.S. Application Data

(60) Provisional application No. 60/949,637, filed on Jul. 13, 2007.

(51) Int. Cl.
| | | |
|---|---|---|
| A61K 39/008 | (2006.01) | |
| C07H 21/04 | (2006.01) | |
| A61K 38/45 | (2006.01) | |
| A61K 39/00 | (2006.01) | |

(52) U.S. Cl.
CPC .............. *A61K 38/45* (2013.01); *A61K 39/008* (2013.01); *A61K 2039/55572* (2013.01)
USPC ...................... 424/192.1; 424/269.1; 536/23.7

(58) Field of Classification Search
CPC ........... A61K 39/008; A61K 2039/552; A61K 2039/55572
USPC ................... 424/192.1, 269.1; 536/23.4, 23.7
See application file for complete search history.

(56) References Cited

U.S. PATENT DOCUMENTS 6,500,437 B1 * 12/2002 Reed et al. ................. 424/269.1

FOREIGN PATENT DOCUMENTS

WO    01/79276 A1    10/2001

OTHER PUBLICATIONS

Peacock et al Nat Genet. Jul. 2007; 39(7): 839-847.*
Pourshafie et al Antimicrob Agents Chemother. Jul. 2004; 48(7): 2409-2414.*
Lederman et al (Molecular Immunology 28:1171-1181, 1991).*
Li et al (Proc. Natl. Acad. Sci. USA 77:3211-3214, 1980).*
Holmes, Exp. Opin.Invest. Drugs, 2001, 10(3):511-519).*
Greenspan et al (Nature Biotechnology, 1999, 7:936-937).*
Houghten et al. (Vaccines, 1986, Edited by Fred Brown: Cold Spring Harbor Laboratory).*

Aebischer et al., "Subunit Vaccination of Mice against New World Cutaneous Leishmaniasis: Comparison of Three Proteins Expressed in Amastigotes and Six Adjuvants," Infection and Immunity 68(3):1328-1336, Mar. 1, 2000.
Aguilar-Be et al., "Cross-Protective Efficacy of a Prophylactic *Leishmania donovani* DNA Vaccine against Visceral and Cutaneous Murine Leishmaniasis," Infection and Immunity 73(2):812-819, Feb. 2005.
Basu et al., "Kinetoplastid Membrane Protein-11 DNA Vaccination Induces Complete Protection against Both Pentavalent Antimonial-Sensitive and -Resistant Strains of *Leishmania donovani* That Correlates with Inducible Nitric Oxide Synthase Activity and IL-4 Generation: Evidence for Mixed Th1- and Th2-Like Responses in Visceral Leishmaniasis," J. Immunol. 174:7160-7171, 2005.
Burns et al., "Molecular characterization of a kinesin-related antigen of *Leishmania chagasi* that detects specific antibody in African and American visceral leishmaniasis," Proc. Natl. Acad. Sci. USA 90:775-779, Jan. 1993.
Ghosh et al., "Immunization with A2 protein results in a mixed Th1/Th2 and a humoral response which protects mice against *Leishmania donovani* infections," Vaccine 20(1-2):59-66, Oct. 12, 2001.
Goto et al., "Cloning, Characterization, and Serodiagnostic Evaluation of *Leishmania infantum* Tandem Repeat Proteins," Infect. Immun. 74(7):3939-3944, Jul. 2006.
Goto et al., "Protective immunization against visceral leishmaniasis using *Leishmania* sterol 24-c-methyltransferase formulated in adjuvant," Vaccine 25(42):7450-7458, Sep. 28, 2007.
Jensen-Pergakes et al., "Sequencing, Disruption, and Characterization of the *Candida albicans* Sterol Methyltransferase (ERG6) Gene: Drug Susceptibility Studies in erg6 Mutants," Antimicrobial Agents and Chemotherapy 42(5):1160-1167, May 1998.
Kaneshiro et al., "*Pneumocystis carinii* erg6 Gene: Sequencing and Expression of Recombinant SAM:Sterol Methyltransferase in Heterologous Systems," J. Eukaryot. Microbiol. Supp.:144S-146S, 2001.
Pourshafie et al., "Cloning of S-Adenosyl-L-Methionine:C-24-Δ-Sterol-Methyltransferase (ERG6) from *Leishmania donovani* and Characterization of mRNAs in Wild-Type and Amphotericin B-Resistant Promastigotes," Antimicrobial Agents and Chemotherapy 48(7):2409-2414, Jul. 2004.
Rafati et al., "Prime-boost vaccination using cysteine proteinases type I and II of *Leishmania infantum* confers protective immunity in murine visceral leishmaniasis," Vaccine 24:2169-2175, 2006.
Stäger et al., "Immunization with a Recombinant Stage-Regulated Surface Protein from *Leishmania donovani* Induces Protection Against Visceral *Leishmaniasis*," Journal of Immunology 165:7064-7071, Jan. 1, 2000.
Tewary et al., "A Heterologous Prime-Boost Vaccination Regimen Using ORFF DNA and Recombinant ORFF Protein Confers Protective Immunity against Experimental Visceral *Leishmaniasis*," J. Infect. Dis. 191:2130-2137, Jun. 15, 2005.
Wilson et al., "A Recombinant *Leishmania chagasi* Antigen That Stimulates Cellular Immune Responses in Infected Mice," Infection and Immunity 63(5):2062-2069, May 1995.

(Continued)

*Primary Examiner* — Padma V Baskar
(74) *Attorney, Agent, or Firm* — Judy Jarecki-Black; Chad Kitchen; Merial Limited

(57) ABSTRACT

Compositions and methods for preventing, treating and detecting leishmaniasis are disclosed. The compositions generally comprise *Leishmania* sterol 24-c-methyltransferase (SMT) polypeptides, portions, variants and/or fusions, as well as polynucleotides encoding SMT polypeptides, portions, variants and/or fusions.

4 Claims, 12 Drawing Sheets

(56) References Cited

OTHER PUBLICATIONS

Zhou et al., "Mechanistic Analysis of a Multiple Product Sterol Methyltransferase Implicated in Ergosterol Biosynthesis in *Trypanosoma brucei*," Journal of Biological Chemistry, 281(10):6290-6296, Mar. 10, 2006.

Search Result Document, "*L. infantum* Protein Sequence Search II," performed Mar. 15, 2007.

Search Result Document, "*L. infantum* Protein Sequence Search," performed Mar. 15, 2007.

Search Result Document, NCBI BLAST Search RID: 1173997078-19887-175375005739.BLASTQ4, performed Mar. 15, 2007.

Search Result Document, NCBI BLAST Search RID: 1173997223-23282-152127865596.BLASTQ2, performed Mar. 15, 2007.

* cited by examiner

```
           10        20        30        40        50
           |         |         |         |         |
  1  MSAGGRETAPTNLIRRRNKDETNGDVSAAADRFRDRFE--KATLEERKAA   LiSMT.PRO
  1  MSAGGRETAPTNLIRRRNKDETNGDVSAAADRFRDRFE--KATLEERKAA   LdSMT.pro
  1  MSAGGRETAPMNLLRRRNKDEINGDVNAAADRFRNRFE--KATLEERKAA   LmSMT.PRO
  1  MSAGARELIPVNLLRRRNKGEANEDVSAAADRFRGRFE--KASLEERKAA   LbSMT.PRO
  1  MSAGAPATLPLNLMRSRRAEEENKDVSTTANRFRERFEGKDASVSGRKAE   TcSMT.PRO 60        70        80        90       100
           |         |         |         |         |
 49  TTTMVNEYYDLVTDFYEYGWGQNFHFAPRYAGETFFESLARHEYFLAARG   LiSMT.PRO
 49  TTTMVNEYYDLVTDFYEYGWGQNFHFAPRYAGETFFESLARHEYFLAARG   LdSMT.pro
 49  TTTMVNEYYDLVTDFYEYGWGQNFHFAPRYAGETFFESLARHEYFLAARG   LmSMT.PRO
 49  TTTMVNEYYDLVTDFYEYGWCQNFHFAPRYAGETFYESIARHEYFLAARG   LbSMT.PRO
 51  TTTMVNEYYDIVTDFYEYGWGQGFHFAPRYLGESLLESLARHEFFLAYQG   TcSMT.PRO 110       120       130       140       150
           |         |         |         |         |
 99  GFMEGDHIVDVGCGVGGPARNMVRLTRCNVIGVNNNDYQISRARRHDALA   LiSMT.PRO
 99  GFMEGDHIVDVGCGVGGPARNMVRLTRCNVIGVNNNDYQISRARRHDALA   LdSMT.pro
 99  GFMEGDHIVDVGCGVGGPARNIVRLTRCNVTGVNNNDYQISRARRHDALA   LmSMT.PRO
 99  GFTENDHIVDIGCGVGGPARNIVRLTRCNITGVNNNDYQITRARRHDASA   LbSMT.PRO
101  QFKPTDTVLDLGCGVGGPARNIVRLAGCNVMGVNNNEYQISRARRHDTKY   TcSMT.PRO 160       170       180       190       200
           |         |         |         |         |
149  GMSSKIDYVKTDFCNMSLADNTFDGAYAIEATCHAKDKVKCYSEVFRVIK   LiSMT.PRO
149  GMSSKIDYVKTDFCNMSLADNTFDGAYAIEATCHAKDKVKCYSEVFRVIK   LdSMT.pro
149  GMSCKIDYVKTDFCNMSLADNTFDGAYAIEATCHAKDKVKCYSEVFRVIK   LmSMT.PRO
149  GMSDKIDYIKTDFCSMSFADNTFDGAYAIEATCHAKDKVKCYSEVFP--R   LbSMT.PRO
151  GMNSKINYTKTDFCNMCFGDNEYDGAYAIEATCHATDKVKCFSEVFRVIK   TcSMT.PRO 210       220       230       240       250
           |         |         |         |         |
199  PGTCFVLYEW--CMTDKYNPNDEYHRTIKHRIELGDGLPEMETCKQVIEY   LiSMT.PRO
199  PGTCFVLYEW--CMTDKYNPNDEYHRTIKHRIELGDGLPEMETCKQVIEY   LdSMT.pro
199  PGTCFVLYEW--CMTDKYNPNDEYHRTIKHRIELGDGLPEMETCKQVIEY   LmSMT.PRO
197  HQIWLLLCPLRVVMTDKYNPDDEYHRKIKHRIELGDGLPEMETAKQVMEY   LbSMT.PRO
201  PGSYFVLYEW--CITEKYDPNNEEHRRIRHKIELGDSLPDLETKGQVIEA   TcSMT.PRO
```

*FIG. 1A*

```
              260       270       280       290       300
              |         |         |         |         |
247  MKQAGFVVEEAIDVISQFESSPIKSIPWYQPLVGDYSSLQGLRSTPIGRI   LiSMT.PRO
247  MKQAGFVVEEAIDVISQFESSPIKSIPWYQPLVGDYSSLQGLRSTPIGRI   LdSMT.pro
247  MKEAGFVVEEAIDVISQFESSPIKSIPWYQPLVGDYSSLQGLRSTPIGRI   LmSMT.PRO
247  MKRAGFMVEEVIDVINQFESSPIKSIPWYQPLTGSYSSLKGVRSTPMGRV   LbSMT.PRO
249  LKASGFIVEDSFDVAERFESSPIHNLPWYLTLQGNYTTLAGLKCSPLGRW   TcSMT.PRO 310       320       330       340       350
              |         |         |         |         |
297  LTNVMCRVLEFARLAPKGTYKATEVLEEAA-----------ESLVVGGQ   LiSMT.PRO
297  LTNVMCRVLEFVRLAPKGTYKATEVLEEAA-----------ESLVVGGQ   LdSMT.pro
297  LTNIMCRVLEFVHLAPKGTYKATEVLEEAA-----------ESLVVGGQ   LmSMT.PRO
297  FTNIMCRVLEFLRLAPKGTHKGDGNSGGGCGKPGDWRPARHLHTVPVHPR   LbSMT.PRO
299  FTNKMCRVLEFAGLAPSGTHKGAEILEEAA-----------RSLVSGGE   TcSMT.PRO 360       370
              |         |
335  LGIFTPSFYIRARKP----SKQA       LiSMT.PRO
335  LGIFTPSFYIRARKP----SKQA       LdSMT.pro
335  LGIFTPSFYIRARKP----SKQA       LmSMT.PRO
347  SQATQRGVVLEVAEE----CRTH       LbSMT.PRO
337  SGIFTPSFFAKARKPLPGEKPRK       TcSMT.PRO
```

*FIG. 1B*

SEQUENCE LISTING

```
<160> NUMBER OF SEQ ID NOS: 12

<210> SEQ ID NO 1
<211> LENGTH: 353
<212> TYPE: PRT
<213> ORGANISM: L. infantum

<400> SEQUENCE: 1

Met Ser Ala Gly Gly Arg Glu Thr Ala Pro Thr Asn Leu Ile Arg Arg
  1               5                  10                  15

Arg Asn Lys Asp Glu Thr Asn Gly Asp Val Ser Ala Ala Ala Asp Arg
                 20                  25                  30

Phe Arg Asp Arg Phe Glu Lys Ala Thr Leu Glu Glu Arg Lys Ala Ala
             35                  40                  45

Thr Thr Thr Met Val Asn Glu Tyr Tyr Asp Leu Val Thr Asp Phe Tyr
 50                  55                  60

Glu Tyr Gly Trp Gly Gln Asn Phe His Phe Ala Pro Arg Tyr Ala Gly
 65                  70                  75                  80

Glu Thr Phe Phe Glu Ser Leu Ala Arg His Glu Tyr Phe Leu Ala Ala
                 85                  90                  95

Arg Gly Gly Phe Met Glu Gly Asp His Ile Val Asp Val Gly Cys Gly
            100                 105                 110

Val Gly Gly Pro Ala Arg Asn Met Val Arg Leu Thr Arg Cys Asn Val
            115                 120                 125

Ile Gly Val Asn Asn Asn Asp Tyr Gln Ile Ser Arg Ala Arg Arg His
130                 135                 140

Asp Ala Leu Ala Gly Met Ser Ser Lys Ile Asp Tyr Val Lys Thr Asp
145                 150                 155                 160

Phe Cys Asn Met Ser Leu Ala Asp Asn Thr Phe Asp Gly Ala Tyr Ala
                165                 170                 175

Ile Glu Ala Thr Cys His Ala Lys Asp Lys Val Lys Cys Tyr Ser Glu
            180                 185                 190

Val Phe Arg Val Ile Lys Pro Gly Thr Cys Phe Val Leu Tyr Glu Trp
            195                 200                 205

Cys Met Thr Asp Lys Tyr Asn Pro Asn Asp Glu Tyr His Arg Thr Ile
        210                 215                 220

Lys His Arg Ile Glu Leu Gly Asp Gly Leu Pro Glu Met Glu Thr Cys
225                 230                 235                 240
```

-continued

```
Lys Gln Val Ile Glu Tyr Met Lys Gln Ala Gly Phe Val Val Glu Glu
                245                 250                 255

Ala Ile Asp Val Ile Ser Gln Phe Glu Ser Ser Pro Ile Lys Ser Ile
            260                 265                 270

Pro Trp Tyr Gln Pro Leu Val Gly Asp Tyr Ser Ser Leu Gln Gly Leu
        275                 280                 285

Arg Ser Thr Pro Ile Gly Arg Ile Leu Thr Asn Val Met Cys Arg Val
    290                 295                 300

Leu Glu Phe Ala Arg Leu Ala Pro Lys Gly Thr Tyr Lys Ala Thr Glu
305                 310                 315                 320

Val Leu Glu Glu Ala Ala Glu Ser Leu Val Val Gly Gly Gln Leu Gly
                325                 330                 335

Ile Phe Thr Pro Ser Phe Tyr Ile Arg Ala Arg Lys Pro Ser Lys Gln
            340                 345                 350

Ala
```

<210> SEQ ID NO 2
<211> LENGTH: 1062
<212> TYPE: DNA
<213> ORGANISM: L. infantum

<400> SEQUENCE: 2

| | | | | | |
|---|---|---|---|---|---|
| atgtccgccg | gtggccgtga | gaccgcgccg | acgaacctga | ttcgtcgccg | caacaaggac | 60 |
| gagacaaacg | gggatgtcag | cgccgccgcc | gaccgcttcc | gcgaccgctt | cgagaaggca | 120 |
| accctcgagg | agcgcaaggc | cgccaccacg | acgatggtca | cgagtactac | gacctggtg  | 180 |
| acggacttct | acgagtacgg | ctggggccag | aacttccatt | tcgcgccgcg | ctacgccggc | 240 |
| gagacctcct | tcgagtccct | cgcgcgccac | gagtacttcc | tggccgctcg | cggcggcttc | 300 |
| atggagggcg | accacatcgt | cgacgtgggc | tgcggcgtcg | gcgtccggc  | gcgcaacatg | 360 |
| gttcgcctca | cgcgctgcaa | cgtcatcggc | gtcaacaaca | acgattacca | gatcagccgc | 420 |
| gctcgccgtc | atgacgcgct | cgccggtatg | agctccaaga | tcgactacgt | caagaccgac | 480 |
| ttctgcaaca | tgagcttagc | cgacaacacc | ttcgacggcg | cctacgccat | cgaggccacc | 540 |
| tgccacgcaa | aggacaaggt | caagtgctat | agcgaggtct | ccgtgtcat  | caagcccggc | 600 |
| acctgctttg | tcctgtacga | gtggtgcatg | accgacaagt | acaaccccaa | tgacgagtac | 660 |
| caccgcacaa | tcaagcaccg | catcgagctg | ggcgacggcc | tgccggagat | ggagacgtgc | 720 |
| aaacaggtga | tcgagtacat | gaagcaggcc | ggcttcgtgg | tggaggaggc | catagacgtc | 780 |
| atcagtcagt | tcgagtccag | ccccatcaag | agtatcccgt | ggtaccagcc | gctggtcggc | 840 |
| gactattcgt | ccctgcaggg | cctgcgctct | accccgattg | gccgcatcct | cacgaacgtc | 900 |
| atgtgtcgcg | tgctggagtt | cgcgcgccta | gctccgaagg | gcacgtacaa | ggcgacggag | 960 |
| gttttggagg | aggctgcgga | aagcctggtg | gtgggcggtc | agctcggcat | cttcacgccg | 1020 |
| tccttctaca | tccgcgctcg | caagccgtcc | aagcaggctt | ag | | 1062 |

<210> SEQ ID NO 3
<211> LENGTH: 353
<212> TYPE: PRT
<213> ORGANISM: L. donovani

<400> SEQUENCE: 3

```
Met Ser Ala Gly Gly Arg Glu Thr Ala Pro Thr Asn Leu Ile Arg Arg
1               5                   10                  15

Arg Asn Lys Asp Glu Thr Asn Gly Asp Val Ser Ala Ala Ala Asp Arg
```

```
                    20                  25                  30
        Phe Arg Asp Arg Phe Glu Lys Ala Thr Leu Glu Glu Arg Lys Ala Ala
                    35                  40                  45

Thr Thr Thr Met Val Asn Glu Tyr Tyr Asp Leu Val Thr Asp Phe Tyr
        50                  55                  60

Glu Tyr Gly Trp Gly Gln Asn Phe His Phe Ala Pro Arg Tyr Ala Gly
        65                  70                  75                  80

Glu Thr Phe Phe Glu Ser Leu Ala Arg His Glu Tyr Phe Leu Ala Ala
                        85                  90                  95

Arg Gly Gly Phe Met Glu Gly Asp His Ile Val Asp Val Gly Cys Gly
                        100                 105                 110

Val Gly Gly Pro Ala Arg Asn Met Val Arg Leu Thr Arg Cys Asn Val
                        115                 120                 125

Ile Gly Val Asn Asn Asn Asp Tyr Gln Ile Ser Arg Ala Arg Arg His
                        130                 135                 140

Asp Ala Leu Ala Gly Met Ser Ser Lys Ile Asp Tyr Val Lys Thr Asp
        145                 150                 155                 160

Phe Cys Asn Met Ser Leu Ala Asp Asn Thr Phe Asp Gly Ala Tyr Ala
                        165                 170                 175

Ile Glu Ala Thr Cys His Ala Lys Asp Lys Val Lys Cys Tyr Ser Glu
                        180                 185                 190

Val Phe Arg Val Ile Lys Pro Gly Thr Cys Phe Val Leu Tyr Glu Trp
                        195                 200                 205

Cys Met Thr Asp Lys Tyr Asn Pro Asn Asp Glu Tyr His Arg Thr Ile
                        210                 215                 220

Lys His Arg Ile Glu Leu Gly Asp Gly Leu Pro Glu Met Glu Thr Cys
        225                 230                 235                 240

Lys Gln Val Ile Glu Tyr Met Lys Gln Ala Gly Phe Val Val Glu Glu
                        245                 250                 255

Ala Ile Asp Val Ile Ser Gln Phe Glu Ser Ser Pro Ile Lys Ser Ile
                        260                 265                 270

Pro Trp Tyr Gln Pro Leu Val Gly Asp Tyr Ser Ser Leu Gln Gly Leu
                        275                 280                 285

Arg Ser Thr Pro Ile Gly Arg Ile Leu Thr Asn Val Met Cys Arg Val
        290                 295                 300

Leu Glu Phe Val Arg Leu Ala Pro Lys Gly Thr Tyr Lys Ala Thr Glu
        305                 310                 315                 320

Val Leu Glu Glu Ala Ala Glu Ser Leu Val Val Gly Gly Gln Leu Gly
                        325                 330                 335

Ile Phe Thr Pro Ser Phe Tyr Ile Arg Ala Arg Lys Pro Ser Lys Gln
                        340                 345                 350

Ala

<210> SEQ ID NO 4
<211> LENGTH: 1062
<212> TYPE: DNA
<213> ORGANISM: L. donovani

<400> SEQUENCE: 4
atgtccgccg gtggccgtga gaccgcgccg acgaacctga ttcgtcgccg caacaaggac    60
gagacaaacg gggatgtcag cgccgccgcc gaccgcttcc gcgaccgctt cgagaaggca   120
accctcgagg agcgcaaggc cgccaccacg acgatggtca cgagtacta cgacctggtg    180 acggacttct acgagtacgg ctggggccag aacttccatt tcgcgccgcg ctacgccggc   240
```

-continued

```
gagaccttct tcgagtccct cgcgcgccac gagtacttcc tggccgctcg cggcggcttc      300
atggagggcg accacatcgt cgacgtgggc tgcggcgtcg gcggtccggc gcgcaacatg      360
gttcgcctca cgcgctgcaa cgtcatcggc gtcaacaaca acgattacca gatcagccgc      420
gctcgccgtc atgacgcgct cgccggtatg agctccaaga tcgactacgt caagaccgac      480
ttctgcaaca tgagcttagc cgacaacacc ttcgacggcg cctacgccat cgaggccacc      540
tgccacgcaa aggacaaggt caagtgctat agcgaggtct tccgtgtcat caagcccggc      600
acctgctttg tcctgtacga gtggtgcatg accgacaagt acaaccccaa tgacgagtac      660
caccgcacaa tcaagcaccg catcgagctg ggcgacggcc tgccggagat ggagacgtgc      720
aaacaggtga tcgagtacat gaagcaggcc ggcttcgtgg tggaggaggc catagacgtc      780
atcagtcagt tcgaatccag ccccatcaag agtatcccgt ggtaccagcc gctggtcggc      840
gactattcgt ccctgcaggg cctgcgctct accccgattg gccgcatcct cacgaacgtc      900
atgtgtcgcg tgctggagtt cgtgcgccta gctccgaagg gcacgtacaa ggcgacggag      960
gttttggagg aggctgcgga aagcctggtg gtgggcggtc agctcggcat cttcacgccg     1020
tccttctaca tccgcgctcg caagccgtcc aagcaggctt ag                        1062
```

<210> SEQ ID NO 5
<211> LENGTH: 353
<212> TYPE: PRT
<213> ORGANISM: L. major

<400> SEQUENCE: 5

```
Met Ser Ala Gly Gly Arg Glu Thr Ala Pro Met Asn Leu Leu Arg Arg
 1               5                  10                  15

Arg Asn Lys Asp Glu Ile Asn Gly Asp Val Asn Ala Ala Ala Asp Arg
            20                  25                  30

Phe Arg Asn Arg Phe Glu Lys Ala Thr Leu Glu Glu Arg Lys Ala Ala
        35                  40                  45

Thr Thr Thr Met Val Asn Glu Tyr Tyr Asp Leu Val Thr Asp Phe Tyr
    50                  55                  60

Glu Tyr Gly Trp Gly Gln Asn Phe His Phe Ala Pro Tyr Ala Gly
65                  70                  75                  80

Glu Thr Phe Phe Glu Ser Leu Ala Arg His Glu Tyr Phe Leu Ala Ala
                85                  90                  95

Arg Gly Gly Phe Met Glu Gly Asp His Ile Val Asp Val Gly Cys Gly
            100                 105                 110

Val Gly Gly Pro Ala Arg Asn Ile Val Arg Leu Thr Arg Cys Asn Val
        115                 120                 125

Thr Gly Val Asn Asn Asn Asp Tyr Gln Ile Ser Arg Ala Arg Arg His
    130                 135                 140

Asp Ala Leu Ala Gly Met Ser Cys Lys Ile Asp Tyr Val Lys Thr Asp
145                 150                 155                 160

Phe Cys Asn Met Ser Leu Ala Asp Asn Thr Phe Asp Gly Ala Tyr Ala
                165                 170                 175

Ile Glu Ala Thr Cys His Ala Lys Asp Lys Val Lys Cys Tyr Ser Glu
            180                 185                 190

Val Phe Arg Val Ile Lys Pro Gly Thr Cys Phe Val Leu Tyr Glu Trp
        195                 200                 205

Cys Met Thr Asp Lys Tyr Asn Pro Asn Asp Glu Tyr His Arg Thr Ile
    210                 215                 220
```

```
Lys His Arg Ile Glu Leu Gly Asp Gly Leu Pro Glu Met Glu Thr Cys
225                 230                 235                 240

Lys Gln Val Ile Glu Tyr Met Lys Glu Ala Gly Phe Val Val Glu Glu
            245                 250                 255

Ala Ile Asp Val Ile Ser Gln Phe Glu Ser Ser Pro Ile Lys Ser Ile
        260                 265                 270

Pro Trp Tyr Gln Pro Leu Val Gly Asp Tyr Ser Ser Leu Gln Gly Leu
    275                 280                 285

Arg Ser Thr Pro Ile Gly Arg Ile Leu Thr Asn Ile Met Cys Arg Val
290                 295                 300

Leu Glu Phe Val His Leu Ala Pro Lys Gly Thr Tyr Lys Ala Thr Glu
305                 310                 315                 320

Val Leu Glu Glu Ala Ala Glu Ser Leu Val Val Gly Gly Gln Leu Gly
            325                 330                 335

Ile Phe Thr Pro Ser Phe Tyr Ile Arg Ala Arg Lys Pro Ser Lys Gln
            340                 345                 350

Ala
```

<210> SEQ ID NO 6
<211> LENGTH: 1062
<212> TYPE: DNA
<213> ORGANISM: L. major

<400> SEQUENCE: 6

```
atgtctgccg gtggccgtga gaccgcgccg atgaacctgc ttcgtcgccg caacaaggat      60
gagataaacg gggatgtcaa cgccgccgcc gaccgcttcc gcaaccgctt cgagaaggca     120
accctcgagg agcgcaaggc cgccaccacg acgatggtca acgagtacta cgacctggtg     180
acggacttct acgagtacgg ctggggccag aactttcatt cgcgccgcg ctacgccggc      240
gagaccttct cgagtccct cgcgcgccac gagtacttcc tggccgcccg cggcggcttc      300
atggagggcg accatatcgt cgacgtgggc tgcggcgtcg cggtccggc gcgcaacata      360
gttcgcctca cgcgctgtaa cgtcaccggc gtcaacaaca cgattacca aatcagccgc      420
gctcgccgtc atgacgcact cgccggtatg agctgcaaaa tcgactacgt caagaccgac     480
ttctgcaaca tgagcttagc cgacaacacc ttcgacggcg cctacgccat cgaggccaca     540
tgccacgcaa aggacaaggt caagtgctat agcgaggtct ccgtgtcat caagcccggc      600
acctgcttcg tcctgtacga gtggtgcatg accgacaagt acaaccccaa tgacgagtac     660
catcgcacga tcaagcaccg cattgagctg ggcgacggcc tgccggagat ggagacgtgc     720
aagcaggtga tcgagtacat gaaggaggcc ggtttcgtgg tggaggaagc catagatgtc     780
atcagtcagt tcgagtccag ccccatcaag agcatcccgt ggtaccagcc gctggttggc     840
gactactcgt cccctgcaggg cctgcgctct accccgattg gcgcatcct caccaacatc     900
atgtgtcgcg tgctggagtt cgtgcaccta gctccgaagg gcacgtacaa ggcgacggag     960
gttttggagg aggctgcgga aagcctggtg gtgggcggtc agctcggcat cttcacgccg    1020
tccttctaca tccgcgctcg caagccgtcc aagcaggcct ag                      1062
```

<210> SEQ ID NO 7
<211> LENGTH: 359
<212> TYPE: PRT
<213> ORGANISM: T. cruzi

<400> SEQUENCE: 7

Met Ser Ala Gly Ala Pro Asp Thr Leu Pro Leu Asn Leu Met Arg Ser

```
            1               5                  10                 15
          Arg Lys Ala Glu Glu Asn Lys Asp Val Ser Thr Thr Ala Asn Arg
                          20                  25                 30

Phe Arg Glu Arg Phe Glu Gly Lys Asp Ala Ser Val Ser Gly Arg Lys
                          35                  40                 45

Ala Glu Thr Thr Thr Met Val Asn Glu Tyr Tyr Asp Ile Val Thr Asp
                  50                  55                  60

Phe Tyr Glu Tyr Gly Trp Gly Gln Cys Phe His Phe Ala Pro Arg Tyr
           65                  70                  75                 80

Leu Gly Glu Ser Leu Leu Glu Ser Leu Ala Arg His Glu Phe Phe Leu
                          85                  90                  95

Ala Tyr Gln Gly Gln Phe Lys Pro Thr Asp Thr Val Leu Asp Leu Gly
                          100                 105                110

Cys Gly Val Gly Gly Pro Ala Arg Asn Ile Val Arg Leu Ala Gly Cys
                          115                 120                125

Asn Val Met Gly Val Asn Asn Asn Glu Tyr Gln Ile Ser Arg Ala Arg
                          130                 135                 140

Arg His Asp Thr Lys Tyr Gly Met Asn Ser Lys Ile Asn Tyr Thr Lys
          145                 150                 155                160

Thr Asp Phe Cys Asn Met Cys Phe Gly Asp Asn Glu Tyr Asp Gly Ala
                              165                 170                 175

Tyr Ala Ile Glu Ala Thr Cys His Ala Thr Asp Lys Val Lys Cys Phe
                          180                 185                 190

Ser Glu Val Phe Arg Val Ile Lys Pro Gly Ser Tyr Phe Val Leu Tyr
                          195                 200                 205

Glu Trp Cys Ile Thr Glu Lys Tyr Asp Pro Asn Asn Glu Glu His Arg
          210                 215                 220

Arg Ile Arg His Lys Ile Glu Leu Gly Asp Ser Leu Pro Asp Leu Glu
          225                 230                 235                 240

Thr Lys Gly Gln Val Ile Glu Ala Leu Lys Ala Ser Gly Phe Ile Val
                              245                 250                 255

Glu Asp Ser Phe Asp Val Ala Glu Arg Phe Glu Ser Ser Pro Ile His
                              260                 265                 270

Asn Leu Pro Trp Tyr Leu Thr Leu Gln Gly Asn Tyr Thr Thr Leu Ala
                              275                 280                 285

Gly Leu Lys Cys Ser Pro Leu Gly Arg Trp Phe Thr Asn Lys Met Cys
                              290                 295                 300

Arg Val Leu Glu Phe Ala Gly Leu Ala Pro Ser Gly Thr His Lys Gly
          305                 310                 315                 320

Ala Glu Ile Leu Glu Glu Ala Ala Arg Ser Leu Val Ser Gly Gly Glu
                              325                 330                 335

Ser Gly Ile Phe Thr Pro Ser Phe Phe Ala Lys Ala Arg Lys Pro Leu
                              340                 345                 350

Pro Gly Glu Lys Pro Arg Lys
                  355

<210> SEQ ID NO 8
<211> LENGTH: 376
<212> TYPE: PRT
<213> ORGANISM: C. albicans

<400> SEQUENCE: 8

Met Ser Pro Val Gln Leu Ala Glu Lys Asn Tyr Glu Arg Asp Glu Gln
           1               5                  10                  15
```

Phe Thr Lys Ala Leu His Gly Glu Ser Tyr Lys Thr Gly Leu Ser
                20                  25                  30

Ala Leu Ile Ala Lys Ser Lys Asp Ala Ala Ser Val Ala Ala Glu Gly
            35                  40                  45

Tyr Phe Lys His Trp Asp Gly Ile Ser Lys Asp Asp Glu Glu Lys
        50                  55                  60

Arg Leu Asn Asp Tyr Ser Gln Leu Thr His His Tyr Tyr Asn Leu Val
65                  70                  75                  80

Thr Asp Phe Tyr Glu Tyr Gly Trp Gly Ser Ser Phe His Phe Ser Arg
                85                  90                  95

Tyr Tyr Lys Gly Glu Ala Phe Arg Gln Ala Thr Ala Arg His Glu His
            100                 105                 110

Phe Leu Ala His Lys Met Asn Leu Asn Glu Asn Met Lys Val Leu Asp
        115                 120                 125

Val Gly Cys Gly Val Gly Gly Pro Gly Arg Glu Ile Thr Arg Phe Thr
130                 135                 140

Asp Cys Glu Ile Val Gly Leu Asn Asn Asn Asp Tyr Gln Ile Glu Arg
145                 150                 155                 160

Ala Asn His Tyr Ala Lys Lys Tyr His Leu Asp His Lys Leu Ser Tyr
                165                 170                 175

Val Lys Gly Asp Phe Met Gln Met Asp Phe Glu Pro Glu Ser Phe Asp
            180                 185                 190

Ala Val Tyr Ala Ile Glu Ala Thr Val His Ala Pro Val Leu Glu Gly
        195                 200                 205

Val Tyr Ser Glu Ile Tyr Lys Val Leu Lys Pro Gly Gly Ile Phe Gly
210                 215                 220

Val Tyr Glu Trp Val Met Thr Asp Lys Tyr Asp Glu Thr Asn Glu Glu
225                 230                 235                 240

His Arg Lys Ile Ala Tyr Gly Ile Glu Val Gly Asp Gly Ile Pro Lys
                245                 250                 255

Met Tyr Ser Arg Lys Val Ala Glu Gln Ala Leu Lys Asn Val Gly Phe
            260                 265                 270

Glu Ile Glu Tyr Gln Lys Asp Leu Ala Asp Val Asp Asp Glu Ile Pro
        275                 280                 285

Trp Tyr Tyr Pro Leu Ser Gly Asp Leu Lys Phe Cys Gln Thr Phe Gly
290                 295                 300

Asp Tyr Leu Thr Val Phe Arg Thr Ser Arg Ile Gly Arg Phe Ile Thr
305                 310                 315                 320

Thr Glu Ser Val Gly Leu Met Glu Lys Ile Gly Leu Ala Pro Lys Gly
                325                 330                 335

Ser Lys Gln Val Thr His Ala Leu Glu Asp Ala Ala Val Asn Leu Val
            340                 345                 350

Glu Gly Gly Arg Gln Lys Leu Phe Thr Pro Met Met Leu Tyr Val Val
        355                 360                 365

Arg Lys Pro Leu Glu Lys Lys Asp
370                 375

<210> SEQ ID NO 9
<211> LENGTH: 28
<212> TYPE: DNA
<213> ORGANISM: Artificial Sequence
<220> FEATURE:
<223> OTHER INFORMATION: primer

<400> SEQUENCE: 9

```
caattacata tgtccgccgg tggccgtg                                        28
```

<210> SEQ ID NO 10
<211> LENGTH: 30
<212> TYPE: DNA
<213> ORGANISM: Artificial Sequence
<220> FEATURE:
<223> OTHER INFORMATION: primer

<400> SEQUENCE: 10

```
ggcaggttcg tccgaatctt cgaaattaac                                      30
```

<210> SEQ ID NO 11
<211> LENGTH: 365
<212> TYPE: PRT
<213> ORGANISM: L. braziliensis

<400> SEQUENCE: 11

```
Met Ser Ala Gly Ala Arg Glu Ile Ile Pro Val Asn Leu Leu Arg Arg
 1               5                  10                  15

Arg Asn Lys Gly Glu Ala Asn Glu Asp Val Ser Ala Ala Ala Asp Arg
                20                  25                  30

Phe Arg Gly Arg Phe Glu Lys Ala Ser Leu Glu Glu Arg Lys Ala Ala
            35                  40                  45

Thr Thr Thr Met Val Asn Glu Tyr Tyr Asp Leu Val Thr Asp Phe Tyr
 50                  55                  60

Glu Tyr Gly Trp Cys Gln Asn Phe His Phe Ala Pro Arg Tyr Ala Gly
 65                  70                  75                  80

Glu Thr Phe Tyr Glu Ser Ile Ala Arg His Glu Tyr Phe Leu Ala Ala
                85                  90                  95

Arg Gly Gly Phe Thr Glu Asn Asp His Ile Val Asp Ile Gly Cys Gly
            100                 105                 110

Val Gly Gly Pro Ala Arg Asn Ile Val Arg Leu Thr Arg Cys Asn Ile
        115                 120                 125

Thr Gly Val Asn Asn Asn Asp Tyr Gln Ile Thr Arg Ala Arg Arg His
130                 135                 140

Asp Ala Ser Ala Gly Met Ser Asp Lys Ile Asp Tyr Ile Lys Thr Asp
145                 150                 155                 160

Phe Cys Ser Met Ser Phe Ala Asp Asn Thr Phe Asp Gly Ala Tyr Ala
                165                 170                 175

Ile Glu Ala Thr Cys His Ala Lys Asp Lys Val Lys Cys Tyr Ser Glu
            180                 185                 190

Val Phe Pro Arg His Gln Thr Trp Leu Leu Cys Pro Leu Arg Val
        195                 200                 205

Val Met Thr Asp Lys Tyr Asn Pro Asp Glu Tyr His Arg Lys Ile
210                 215                 220

Lys His Arg Ile Glu Leu Gly Asp Gly Leu Pro Glu Met Glu Thr Ala
225                 230                 235                 240

Lys Gln Val Val Glu Tyr Met Lys Arg Ala Gly Phe Met Val Glu Glu
                245                 250                 255

Val Ile Asp Val Ile Asn Gln Phe Glu Ser Ser Pro Ile Lys Ser Ile
            260                 265                 270

Pro Trp Tyr Gln Pro Leu Thr Gly Ser Tyr Ser Ser Leu Lys Gly Val
        275                 280                 285

Arg Ser Thr Pro Met Gly Arg Val Phe Thr Asn Ile Met Cys Arg Val
    290                 295                 300
```

-continued

```
Leu Glu Phe Leu Arg Leu Ala Pro Lys Gly Thr His Lys Gly Asp Gly
305                 310                 315                 320

Asn Ser Gly Gly Gly Cys Gly Lys Pro Gly Asp Trp Arg Pro Ala Arg
                325                 330                 335

His Leu His Thr Val Pro Val His Pro Arg Ser Gln Ala Thr Gln Arg
            340                 345                 350

Gly Val Val Leu Glu Val Ala Glu Glu Cys Arg Thr His
        355                 360                 365

<210> SEQ ID NO 12
<211> LENGTH: 1098
<212> TYPE: DNA
<213> ORGANISM: L. braziliensis

<400> SEQUENCE: 12
atgtcggcag gtgctcgtga gatcattccg gtaaacctgc ttcgtcgccg caacaagggt     60
gaagcgaacg aggatgtcag cgccgccgcc gaccgcttcc gcggccgctt cgagaaggca    120
agcctcgaag aacgcaaggc cgccactacg acgatggtca acgagtacta tgacctggtg    180
actgatttct acgagtacgg ctggtgccag aactttcatt tcgcgcctcg ctacgctggc    240
gagaccttct acgagtccat cgcgcgccac gagtacttcc tggccgcacg cggtggcttc    300
acggagaacg accacatcgt cgacatcggc tgcggcgtcg gcggcccggc acgcaacatt    360
gtgcgcctca cgcgctgcaa catcaccggc gtaaacaaca acgattacca gatcacccgt    420
gcacgccgcc atgatgcgag cgccggtatg agcgacaaaa tcgactacat taagaccgac    480
ttctgtagca tgagctttgc cgacaacacc ttcgacggcg cctacgccat tgaggccacc    540
tgccacgcaa aggacaaggt caagtgctac agcgaggtct tcccgcgtca tcaaacctgg    600
ctcctgcttt gtcctttacg agtggtgatg accgataagt acaaccccga cgacgagtac    660
catcgcaaga tcaagcaccg catcgagctg ggcgatggcc tgccggagat ggagacggcc    720
aagcaggtgg tggagtacat gaagcgggcc ggttttatgg tagaggaggt catagacgtc    780
attaaccagt ttgagtccag ccctatcaag agtatcccgt ggtaccagcc gctgaccggt    840
agctattcat ctctgaaagg cgtgcgctcc accccgatgg gccgcgtttt caccaacatc    900
atgtgccgtg tgctggagtt cctacgcctg gctccgaagg gcacacacaa gggcgacgga    960
aattctggag gaggctgcgg aaagcctggc gattggcggc cggctcggca tcttcacacc   1020
gtccctgtac atccgcgctc gcaagccact caaagaggtg tagttctcga ggttgccgaa   1080
gaatgccgaa cacactga                                                 1098
```

LEISHMANIA STEROL 24-C-METHYLTRANSFERASE COMPOSITIONS FOR THE PREVENTION, TREATMENT AND DIAGNOSIS OF LEISHMANIASIS

STATEMENT OF GOVERNMENT INTEREST

This invention was made with government support under Grant No. AI-025038 awarded by the National Institutes of Health. The government has certain rights in this invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 480239_404_SEQUENCE_LISTING.txt. The text file is 20 KB; it was created on Jul. 11; 2008; and it is being submitted electronically via EFS-Web, concurrent with the filing of the specification.

BACKGROUND OF THE INVENTION

1. Field of the Invention

The present invention relates generally to compositions and methods for preventing, treating and detecting leishmaniasis in patients. More particularly, the invention relates to compositions comprising Leishmania sterol 24-c-methyltransferase (SMT) polypeptides, fusion polypeptides thereof, as well as polynucleotides encoding such polypeptides and fusions.

2. Background of the Related Art

Human leishmaniasis is a spectrum of diseases caused by protozoan parasites of the genus *Leishmania*. Leishmaniases are roughly classified into three types of diseases, cutaneous leishmaniasis (CL), mucosal leishmaniasis (ML) and visceral leishmaniasis (VL), according to the clinical manifestations. Visceral leishmaniasis, generally caused by species of the *L. donovani* complex, i.e., *L. donovani* and *L. infantum (chagasi)*, is the most severe form, with approximately 500,000 new cases reported annually (information from World Health Organization: www dot who dot int/leishmaniasis/en/). Active VL is characterized by hematological and hepatosplenic abnormalities, and is generally fatal unless properly treated.

*Leishmania* parasites are transmitted by the bite of sandflies and the infecting promastigotes differentiate into and replicate as amastigotes within macrophages in the mammalian host. In common with other intracellular pathogens, cellular immune responses are critical for protection against leishmaniasis. Th1 immune responses play an important role in mediating protection against *Leishmania*, including roles for $CD4^+$ and $CD8^+$ T cells, IFN-$\gamma$, IL-12, TNF-$\alpha$ and NO, whereas inhibitory effects have been reported for IL-10 and TGF-$\beta$ (Engwerda et al., (1998) *Eur J Immunol* 28:669-680; Murphy et al., (2001) *Eur J Immunol* 31:2848-2856; Murray and Nathan. (1999) *J Exp Med* 189:741-746; Murray et al., (2000) *Infect Immun* 68:6289-6293; Squires et al., (1989) J Immunol 143:4244-4249; Taylor and Murray. (1997) *J Exp Med* 185:1231-1239; Kaye and Bancroft. (1992) *Infect Immun* 60:4335-4342; Stern et al., (1988) *J Immunol* 140:3971-3977; and Wilson et al., (1998) *J Immunol* 161:6148-6155). Immunization against leishmaniasis in animal models can be effected by delivery of antigen-encoding DNA vectors (Gurunathan et al., (1997) *J Exp Med* 186:1137-1147; Piedrafita et al., (1999) *J Immunol* 163:1467-1472; and Mendez et al., (2001) *J Immunol* 166:5122-5128) or by administration of proteins formulated with Th1-inducing adjuvants including IL-12 (Afonso et al., (1994) *Science* 263:235-237; Stobie et al., (2000) *Proc Natl Acad Sci USA* 97:8427-8432; and Kenney et al., (1999) *J Immunol* 163:4481-4488) or TLR ligands such as CpG oligonucleotides (Rhee et al., (2002) *J Exp Med* 195:1565-1573; Stacey and Blackwell. (1999) *Infect Immun* 67:3719-3726; and Walker et al., (1999) *Proc Natl Acad Sci USA* 96:6970-6975) and monophosphoryl lipid A (Coler et al., (2002) *Infect Immun* 70:4215-4225 and Skeiky et al., (2002) *Vaccine* 20:3292-3303).

In spite of evidence that sub-unit vaccines may be effective in models of VL (Basu et al., (2005) *J Immunol* 174:7160-7171; Stager et al., (2000) *J Immunol* 165:7064-7071; Ghosh et al., (2001) *Vaccine* 20:59-66; Wilson et al., (1995) *Infect Immun* 63:2062-2069; Tewary et al., (2005) *J Infect Dis* 191: 2130-2137; Aguilar-Be et al., (2005) *Infect Immun* 73:812-819; and Rafati et al., (2006) *Vaccine* 24:2169-2175), progress toward defining bona fide antigen candidates effective against VL in vivo has been lacking Several *L. infantum* antigens have been identified by serological screening using sera from *L. infantum*-infected hamsters (Goto et al., (2006) *Infect Immun* 74:3939-3944). Sterol 24-c-methyltransferase (SMT), one of the antigens found to be reactive, is an enzyme involved in biosynthesis of ergosterol, which is a target molecule of leishmanicidal and fungicidal amphotericin B (Pourshafie et al., (2004) *Antimicrob Agents Chemother* 48:2409-2414). Amphotericin B shows selective killing activity selectively against some protozoan parasites and fungi, as ergosterol is not found in mammalian cells. Similarly, SMT is found in several parasites, fungi and plants, but is absent in mammals.

Strategies employing vaccines consisting of whole organisms for preventing or treating leishmaniasis have not been effective in humans. Accordingly, there remains a significant need for immunogenic compositions and vaccines that can effectively prevent and/or treat leishmaniasis in humans and other mammals (e.g., canines). The present invention fulfills these needs and offers other related advantages

SUMMARY OF THE INVENTION

Briefly stated, the present invention provides compositions and methods for preventing, treating and detecting leishmaniasis. In one aspect, compositions of the invention employ polypeptides comprising at least an immunogenic portion of a *Leishmania* sterol 24-c-methyltransferase (SMT) polypeptide, or a variant thereof, wherein the portion or variant retains the desired immunogenic properties of a full length SMT polypeptide. In a more particular embodiment, the *Leishmania* SMT polypeptide comprises an amino acid sequence of an *L. donovani, L. infantum, L. major,* or *L. braziliensis* SMT polypeptide. In a more specific embodiment, the SMT polypeptide comprises an amino acid sequence set forth in any one of SEQ ID NOs: 1, 3, 5, and 11.

In another aspect of the invention, compositions comprising polynucleotides encoding the above polypeptides are provided, as well as recombinant expression vectors comprising these polynucleotide sequences and host cells transformed or transfected with such expression vectors. In a more particular embodiment, the polynucleotide comprises a nucleic acid sequence encoding an *L. donovani, L. infantum, L. major,* or *L. braziliensis* SMT polypeptide. In a more specific embodiment, the SMT polynucleotide comprises a nucleic acid sequence set forth in any one of SEQ ID NOs: 2, 4, 6, and 12.

In another aspect, the present invention provides a fusion polypeptide comprising at least an immunogenic portion of a *Leishmania* SMT antigen, and further comprising one or more heterologous fusion partners. In a related aspect, polynucleotides encoding such fusion proteins are also provided In yet another aspect, the invention provides pharmaceutical compositions which comprise one or more of the polypeptides and/or fusion polypeptides described herein, or a polynucleotide encoding such polypeptides, in combination with a physiologically acceptable carrier.

In another aspect of the invention, vaccine compositions are provided which comprise one or more of the polypeptides and/or fusion polypeptides described herein, or a polynucleotide encoding such polypeptides, in combination with an immunostimulant. In a more particular embodiment, the immunostimulant is an adjuvant that induces a predominately Th1 type immune response.

In further aspects, the present invention provides methods for stimulating a cellular and/or humoral immune response in a patient, comprising administering to a patient a pharmaceutical composition or vaccine as described above.

In another aspect, the present invention provides methods for inducing protective immunity against leishmaniasis in a patient, comprising administering to a patient a pharmaceutical composition or vaccine as described above.

In a related aspect, methods are provided for treating a patient afflicted with leishmaniasis, comprising administering to a patient a pharmaceutical composition or vaccine as described above.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 1 shows the amino acid sequence alignment of SMTs from *L. infantum* (SEQ ID NO: 1), *L. donovani* (SEQ ID NO: 3), *L. major* (SEQ ID NO: 5), *T. cruzi* (SEQ ID NO: 7) and *L. braziliensis* (SEQ ID NO: 11), as deduced from their corresponding cDNA sequences. Residues matching with *L. infantum* SMT are shown in boxes.

DESCRIPTION OF SEQUENCE IDENTIFIERS

Figure 2:
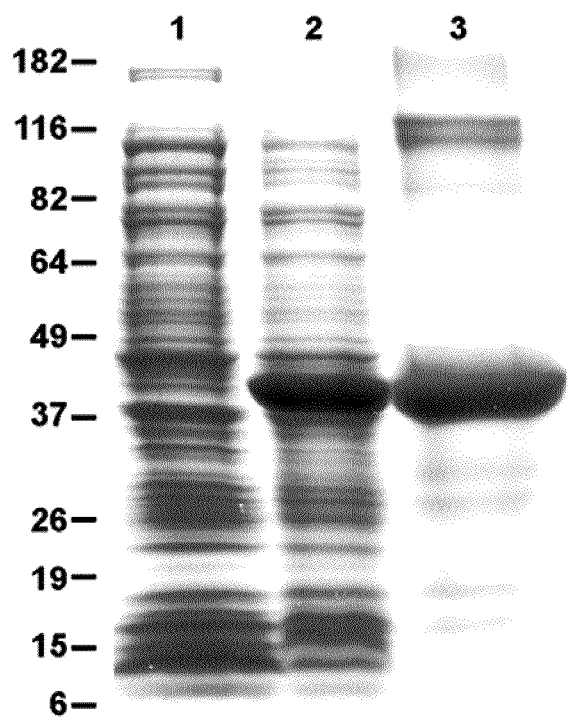
FIG. 2 shows a Coomassie blue stained SDS/4-20% polyacrylamide gradient gels of uninduced *E. coli* lysates (lane 1), induced lysates (lane 2) and purified *L. infantum* SMT (lane 3). Sizes are shown in kDa on the left.

SEQ ID NO: 1 is the amino acid sequence for the *L. infantum* sterol 24-c-methyltransferase (SMT) polypeptide.

SEQ ID NO: 2 is a nucleic acid sequence encoding the polypeptide of SEQ ID NO: 1.

SEQ ID NO: 3 is the amino acid sequence for the *L. donovani* sterol 24-c-methyltransferase (SMT) polypeptide.

SEQ ID NO: 4 is a nucleic acid sequence encoding the polypeptide of SEQ ID NO: 3.

SEQ ID NO: 5 is the amino acid sequence for the *L. major* sterol 24-c-methyltransferase (SMT) polypeptide.

SEQ ID NO: 6 is a nucleic acid sequence encoding the polypeptide of SEQ ID NO: 5.

SEQ ID NO: 7 is the amino acid sequence for the *T. cruzi* sterol 24-c-methyltransferase (SMT) polypeptide.

SEQ ID NO: 8 is the amino acid sequence for the *C. albicans* sterol 24-c-methyltransferase (SMT) polypeptide.

SEQ ID NOs: 9-10 are primers used to amplify an open reading frame from *L. infantum* SMT.

SEQ ID NO: 11 is the amino acid sequence for the *L. braziliensis* sterol 24-c-methyltransferase (SMT) polypeptide.

SEQ ID NO: 12 is a nucleic acid sequence encoding the polypeptide of SEQ ID NO: 11.

DETAILED DESCRIPTION OF THE INVENTION

As noted above, the present invention is generally directed to compositions and methods for preventing, treating and detecting leishmaniasis. The compositions of the invention include, for example, polypeptides that comprise at least an immunogenic portion of a *Leishmania* sterol 24-c-methyltransferase (SMT) polypeptide, or a variant of such a polypeptide, wherein the portion or variant retain substantially the same or similar immunogenic properties as a full length SMT polypeptide. As further demonstrated herein, immunization strategies using compositions of the invention provide significant in vivo protection against *L. infantum*, a causative agent of VL in humans and dogs. Further, the prophylactic effect achieved using compositions of the invention shows substantial improvements and advantages relative to previously reported vaccine strategies.

As used herein, the term "polypeptide" encompasses amino acid chains of any length, including full length proteins, wherein the amino acid residues are linked by covalent bonds. A polypeptide comprising an immunogenic portion of an SMT polypeptide may consist solely of an immunogenic portion, may contain two or more immunogenic portions and/or may contain additional sequences. The additional sequences may be derived from a native *Leishmania* SMT polypeptide or may be heterologous, and such heterologous sequences may (but need not) be immunogenic.

An immunogenic portion of a *Leishmania* SMT polypeptide is a portion that is capable of eliciting an immune response (i.e., cellular and/or humoral) in a presently or previously *Leishmania*-infected patient (such as a human or a dog) and/or in cultures of lymph node cells or peripheral blood mononuclear cells (PBMC) isolated from presently or previously *Leishmania*-infected individuals. The cells in which a response is elicited may comprise a mixture of cell types or may contain isolated component cells (including, but not limited to, T-cells, NK cells, macrophages, monocytes and/or B cells). In a particular embodiment, immunogenic portions are capable of inducing T-cell proliferation and/or a dominantly Th1-type cytokine response (e.g., IL-2, IFN-γ, and/or TNF-α production by T-cells and/or NK cells; and/or IL-12 production by monocytes, macrophages and/or B cells). Immunogenic portions of the antigens described herein may generally be identified using techniques known to those of ordinary skill in the art, including the representative methods provided herein.

Immunogenic portions of an SMT polypeptide can be essentially any length provided they retain one or more of the immunogenic regions of SMT that are responsible for and/or contribute to the in vivo protection provided against leishmaniasis by the full length SMT polypeptide, as disclosed herein. In one embodiment, the ability of an immunogenic portion to react with antigen-specific antisera may be enhanced or unchanged, relative to the native protein, or may be diminished by less than 50%, and preferably less than 20%, relative to the native protein. Illustrative portions will generally be at least 10, 15, 25, 50, or 100 amino acids in length, or more, up to and including full length SMT polypeptide. In a particular embodiment, an immunogenic portion of an SMT polypeptide is one capable of providing protection, for example in an in vivo assay as described herein, against a *Leishmania* species from the *L. donovani* complex, i.e. *L. donovani* and/or *L. infantum*, which are believed to be causative agents of VL in humans and dogs.

The compositions and methods of the present invention also encompass variants of the above polypeptides. A polypeptide "variant," as used herein, is a polypeptide that differs from a native protein in one or more substitutions, deletions, additions and/or insertions, such that the desired immunogenicity of the variant polypeptide is not substantially diminished relative to a native SMT polypeptide. In one embodiment, the ability of a variant to react with antigen-specific antisera may be enhanced or unchanged, relative to the native protein, or may be diminished by less than 50%, and preferably less than 20%, relative to the native protein. In a particular embodiment, a variant of an SMT polypeptide is one capable of providing protection, for example in an in vivo assay as described herein, against a *Leishmania* species from the *L. donovani* complex, i.e. *L. donovani* and/or *L. infantum*.

Variants may generally be identified by modifying one of the above polypeptide sequences and evaluating the reactivity of the modified polypeptide with antigen-specific antibodies or antisera as described herein or by performing an in vivo protection assay as described herein.

Polypeptide variants will generally include those exhibiting at least about 70%, 75%, 80%, 85%, 90%, 91%, 92%, 93%, 94%, 95%, 96%, 97%, 98%, 99% or more identity (for example, determined as described below) to an SMT polypeptide disclosed herein.

In certain embodiments, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a particular embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

Polynucleotides may comprise a native sequence (i.e., an endogenous sequence that encodes a protein or a portion thereof) or may comprise a variant, or a biological or antigenic functional equivalent of such a sequence. Polynucleotide variants may contain one or more substitutions, additions, deletions and/or insertions, as further described below, preferably such that the immunogenicity of the encoded polypeptide is not substantially diminished, relative to a native tumor protein. The effect on the immunogenicity of the encoded polypeptide may generally be assessed as described herein.

When comparing polynucleotide or polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Alignment of sequences for comparison may be conducted using, for example, the Megalign program in the Lasergene suite of bioinformatics software (DNASTAR, Inc., Madison, Wis.) using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein (1990) Unified Approach to Alignment and Phylogenes pp. 626-645 *Methods in Enzymology* vol. 183, Academic Press, Inc., San Diego, Calif.; Higgins and Sharp (1989) *CABIOS* 5:151-153; Myers, E. W. and Muller W. (1988) *CABIOS* 4:11-17; Robinson, E. D. (1971) *Comb. Theor* 11:105; Santou, N. Nes, M. (1987) *Mol. Biol. Evol.* 4:406-425; Sneath and Sokal (1973) *Numerical Taxonomy—the Principles and Practice of Numerical Taxonomy*, Freeman Press, San Francisco, Calif.; Wilbur and Lipman (1983) *Proc. Natl. Acad., Sci. USA* 80:726-730.

Alternatively, alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=−4 and a comparison of both strands.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Therefore, the present invention encompasses polynucleotide and polypeptide sequences having substantial identity to the sequences disclosed herein, for example those comprising at least 70%, 75%, 80%, 85%, 90%, 95%, 96%, 97%, 98%, or 99% or higher, sequence identity compared to a polynucleotide or polypeptide sequence of this invention using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning, and the like.

In additional embodiments, the present invention provides isolated polynucleotides and polypeptides comprising various lengths of contiguous stretches of sequence identical to or complementary to one or more of the sequences disclosed herein. For example, polynucleotides are provided by this invention that comprise at least about 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative DNA segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

In other embodiments, the present invention is directed to polynucleotides that are capable of hybridizing under moderately stringent conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

Moreover, it will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

In another aspect of the invention, fusion polypeptides are provided that comprise at least an immunogenic portion of an SMT polypeptide and further comprising a heterologous fusion partner, as well as polynucleotides encoding such fusion polypeptides. For example, in one embodiment, a fusion polypeptide comprises one or more immunogenic portions of an SMT polypeptide and one or more additional immunogenic *Leishmania* sequences, which are joined via a peptide linkage into a single amino acid chain. In another embodiment, a fusion polypeptide may comprise multiple *Leishmania* antigenic epitopes wherein at least one of the epitopes is from an SMT polypeptide. As used herein an "epitope" is a portion of an antigen that reacts with blood samples from *Leishmania*-infected individuals (i.e., an epitope is specifically bound by one or more antibodies and/or T-cells present in such blood samples.

In another embodiment, a heterologous fusion partner comprises a sequence that assists in providing T helper epitopes (an immunological fusion partner), preferably T helper epitopes recognized by humans, or that assists in expressing the protein (an expression enhancer) at higher yields than the native recombinant protein. Certain preferred fusion partners include both immunological and expression-enhancing fusion partners. Other fusion partners may be selected so as to increase the solubility of the protein or to enable the protein to be targeted to desired intracellular compartments. Still further fusion partners include affinity tags, which facilitate purification of the protein.

Within a particular embodiment, an immunological fusion partner comprises a sequence derived from protein D, a surface protein of the gram-negative bacterium *Haemophilus influenza* B (WO 91/18926). For example, one protein D derivative comprises approximately the first third of the protein (e.g., the first N-terminal 100 110 amino acids), and a protein D derivative may be lipidated. Within certain embodiments, the first 109 residues of a lipoprotein D fusion partner is included on the N-terminus to provide the polypeptide with additional exogenous T cell epitopes and to increase the expression level in *E. coli* (thus functioning as an expression enhancer). The lipid tail ensures optimal presentation of the antigen to antigen presenting cells. Other illustrative fusion partners include the non-structural protein from influenzae virus, NS1 (hemaglutinin) Typically, the N-terminal 81 amino acids are used, although different fragments that include T-helper epitopes may also be used.

In another particular embodiment, an immunological fusion partner comprises an amino acid sequence derived from the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* (1986) 43:265-292). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* (1992) 10:795-798). Within a particular embodiment, a repeat portion of LYTA may be incorporated into a fusion protein. A repeat portion is found in the C-terminal region starting at residue 178. A more particular repeat portion incorporates residues 188-305.

Fusion sequences may be joined directly (i.e., with no intervening amino acids) or may be joined by way of a linker sequence (e.g., Gly-Cys-Gly) that does not significantly diminish the immunogenic properties of the component polypeptides. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order. Fusion polypeptides or fusion proteins can also include conservatively modified variants, polymorphic variants, alleles, mutants, subsequences, interspecies homologs, and immunogenic fragments of the antigens that make up the fusion protein.

Fusion polypeptides may generally be prepared using standard techniques, including recombinant technology, chemical conjugation, and the like. For example, DNA sequences encoding the polypeptide components of a fusion may be assembled separately and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in frame. This permits translation into a single fusion polypeptide that retains the biological activity of the component polypeptides.

A peptide linker sequence may be employed to separate the fusion components by a distance sufficient to ensure that each polypeptide folds into its desired secondary and/or tertiary structures. Such a peptide linker sequence may be incorporated into the fusion polypeptide using standard techniques well known in the art. Suitable peptide linker sequences may be chosen, for example, based on one or more of the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Certain preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., (1985) *Gene* 40:39-46,; Murphy et al., (1986) *Proc. Natl. Acad. Sci. USA* 83:8258-8262; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

In general, polypeptides and fusion polypeptides (as well as their encoding polynucleotides) are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Leishmania SMT polypeptides and polynucleotides of the invention may be prepared or isolated using any of a variety of procedures and using any of a variety of Leishmania species including, but not limited to, L. donovani, L. chagasi, L. infantum, L. major, L. amazonensis, L. braziliensis, L. panamensis, L. mexicana, L. tropica, and L. guyanensis. Such species are available, for example, from the American Type Culture Collection (ATCC), Rockville, Md.

Regardless of the method of preparation, the SMT polypeptides described herein are preferably immunogenic. In other words, the polypeptides (and immunogenic portions thereof) are capable of eliciting an immune response in cultures of lymph node cells and/or peripheral blood mononuclear cells (PBMC) isolated from presently or previously Leishmania-infected individuals. More specifically, the antigens, and immunogenic portions thereof, have the ability to induce T-cell proliferation and/or to elicit a dominantly Th1-type cytokine response (e.g., IL-2, IFN-γ, and/or TNF-α production by T-cells and/or NK cells; and/or IL-12 production by monocytes, macrophages and/or B cells) in cells isolated from presently or previously *Leishmania*-infected individuals. A *Leishmania*-infected individual may be afflicted with a form of leishmaniasis (such as subclinical, cutaneous, mucosal or active visceral) or may be asymptomatic. Such individuals may be identified using methods known to those of ordinary skill in the art. Individuals with leishmaniasis may be identified based on clinical findings associated with at least one of the following: isolation of parasite from lesions, a positive skin test with *Leishmania* lysate or a positive serological test. Asymptomatic individuals are infected individuals who have no signs or symptoms of the disease. Such individuals can be identified based on a positive serological test and/or skin test with *Leishmania* lysate.

The term "PBMC," which refers to a preparation of nucleated cells consisting primarily of lymphocytes and monocytes that are present in peripheral blood, encompasses both mixtures of cells and preparations of one or more purified cell types. PBMC may be isolated by methods known to those in the art. For example, PBMC may be isolated by density centrifugation through, for example, Ficoll™ (Winthrop Laboratories, New York). Lymph node cultures may generally be prepared by immunizing BALB/c mice (e.g., in the rear foot pad) with *Leishmania* promastigotes emulsified in complete Freünd's adjuvant. The draining lymph nodes may be excised following immunization and T-cells may be purified in an anti-mouse Ig column to remove the B cells, followed by a passage through a Sephadex G10 column to remove the macrophages. Similarly, lymph node cells may be isolated from a human following biopsy or surgical removal of a lymph node.

The ability of a *Leishmania* SMT polypeptide, or a portion, variant or fusion thereof, to induce a response in PBMC or lymph node cell cultures may be evaluated, for example, by contacting the cells with the polypeptide and measuring a suitable response. In general, the amount of polypeptide that is sufficient for the evaluation of about $2\times10^5$ cells ranges from about 10 ng to about 100 μg, and preferably is about 1-10 μg. The incubation of polypeptide with cells is typically performed at 37° C. for about 1-3 days. Following incubation with polypeptide, the cells are assayed for an appropriate response. If the response is a proliferative response, any of a variety of techniques well known to those of ordinary skill in the art may be employed. For example, the cells may be exposed to a pulse of radioactive thymidine and the incorporation of label into cellular DNA measured. In general, a polypeptide that results in at least a three fold increase in proliferation above background (i.e., the proliferation observed for cells cultured without polypeptide) is considered to be able to induce proliferation.

Alternatively, the response to be measured may be the secretion of one or more cytokines (such as interferon-γ (IFN-γ), interleukin-4 (IL-4), interleukin-12 (p70 and/or p40), interleukin-2 (IL-2) and/or tumor necrosis factor-α (TNF-α)) or the change in the level of mRNA encoding one or more specific cytokines. For example, the secretion of interferon-γ, interleukin-2, tumor necrosis factor-α and/or interleukin-12 is indicative of a Th1 response, which is responsible for the protective effect against *Leishmania*. Assays for any of the above cytokines may generally be performed using methods known to those of ordinary skill in the art, such as an enzyme-linked immunosorbent assay (ELISA). Suitable antibodies for use in such assays may be obtained from a variety of sources such as Chemicon, Temucula, Calif. and PharMingen, San Diego, Calif., and may generally be used according to the manufacturer's instructions. The level of mRNA encoding one or more specific cytokines may be evaluated by, for example, amplification by polymerase chain reaction (PCR). In general, a polypeptide that is able to induce, in a preparation of about $1\text{-}3\times10^5$ cells, the production of 30 pg/mL of IL-12, IL-4, IFN-γ, TNF-α or IL-12 p40, or 10 pg/mL of IL-12 p70, is considered able to stimulate production of a cytokine Immunogenic portions of a *Leishmania* SMT polypeptide may be prepared and evaluated using well known techniques, such as those summarized in Paul, Fundamental Immunology, 3rd ed., 243-247 (Raven Press, 1993) and references cited therein. Such techniques include screening polypeptides derived from the native antigen for immunogenic properties using, for example, a representative techniques described herein.

In addition to recombinant polypeptide expression, SMT polypeptides, portions and variants may be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, (1963) *J. Am. Chem. Soc.* 85:2149-2146. Equipment for automated synthesis of polypeptides is commercially available from suppliers such as Perkin Elmer/Applied BioSystems Division, Foster City, Calif., and may be operated according to the manufacturer's instructions.

Recombinant polypeptides containing portions and/or variants of a native SMT polypeptide may be readily prepared from a DNA sequence encoding the antigen, using well known and established techniques. For example, supernatants from suitable host/vector systems which secrete recombinant protein into culture media may be first concentrated using a commercially available filter. Following concentration, the concentrate may be applied to a suitable purification matrix such as an affinity matrix or an ion exchange resin.

In general, any of a variety of expression vectors known to those of ordinary skill in the art may be employed to express recombinant polypeptides of this invention. Expression may be achieved in any appropriate host cell that has been transformed or transfected with an expression vector containing a polynucleotide that encodes a recombinant polypeptide. Suitable host cells include prokaryotes, yeast and higher eukaryotic cells. Preferably, the host cells employed are E. coli, yeast or a mammalian cell line such as COS or CHO. The DNA sequences expressed in this manner may encode naturally occurring antigens, portions of naturally occurring antigens, or other variants thereof. For example, variants of a native antigen may generally be prepared using standard mutagenesis techniques, such as oligonucleotide-directed site-specific mutagenesis, and sections of the DNA sequence may be removed to permit preparation of truncated polypeptides.

In certain aspects, the polypeptides, polynucleotides, portions, variants, fusion polypeptides, etc., as described herein, are incorporated into pharmaceutical compositions or vaccines. Pharmaceutical compositions generally comprise one or more polypeptides, polynucleotides, portions, variants, fusion polypeptides, etc., as described herein, in combination with a physiologically acceptable carrier. Vaccines, also referred to as immunogenic compositions, generally comprise one or more of the polypeptides, polynucleotides, portions, variants, fusion proteins, etc., as described herein, in combination with an immunostimulant, such as an adjuvant.

An immunostimulant may be any substance that enhances or potentiates an immune response (antibody and/or cell-mediated) to an exogenous antigen. Examples of immunostimulants include adjuvants, biodegradable microspheres (e.g., polylactic galactide) and liposomes (into which the compound is incorporated; see, e.g., Fullerton, U.S. Pat. No. 4,235,877). Vaccine preparation is generally described in, for example, Powell & Newman, eds., Vaccine Design (the subunit and adjuvant approach) (1995).

Any of a variety of immunostimulants may be employed in the vaccines of this invention. For example, an adjuvant may be included. Many adjuvants contain a substance designed to protect the antigen from rapid catabolism, such as aluminum hydroxide or mineral oil, and a stimulator of immune responses, such as lipid A (natural or synthetic), Bortadella pertussis or Mycobacterium species or Mycobacterium-derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 and derivatives thereof (GlaxoSmithKline Beecham, Philadelphia, Pa.); CWS, TDM, Leif, aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Other illustrative adjuvants useful in the context of the invention include Toll-like receptor agonists, such as TLR7 agonists, TLR7/8 agonists, and the like. Still other illustrative adjuvants include imiquimod, gardiquimod, resiquimod, and related compounds.

Certain preferred vaccines employ adjuvant systems designed to induce an immune response predominantly of the Th1 type. High levels of Th1-type cytokines (e.g., IFN-γ, TNF-α, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mossman and Coffman, (1989) Ann. Rev. Immunol. 7:145-173.

Certain adjuvants for use in eliciting a predominantly Th1-type response include, for example, a combination of monophosphoryl lipid A, preferably 3-de-O-acylated monophosphoryl lipid A (3D-MPL® adjuvant), together with an aluminum salt (U.S. Pat. Nos. 4,436,727; 4,877,611; 4,866,034; and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., (1996) Science 273:352. Another illustrative adjuvant comprises a saponin, such as Quil A, or derivatives thereof, including QS21 and QS7 (Aquila Biopharmaceuticals Inc., Framingham, Mass.); Escin; Digitonin; or Gypsophila or Chenopodium quinoa saponins Other illustrative formulations include more than one saponin in the adjuvant combinations of the present invention, for example combinations of at least two of the following group comprising QS21, QS7, Quil A, β-escin, or digitonin.

In a particular embodiment, the adjuvant system includes the combination of a monophosphoryl lipid A and a saponin derivative, such as the combination of QS21 and 3D-MPL® adjuvant, as described in WO 94/00153, or a less reactogenic composition where the QS21 is quenched with cholesterol, as described in WO 96/33739. Other formulations comprise an oil-in-water emulsion and tocopherol. Another adjuvant formulation employing QS21, 3D-MPL® adjuvant and tocopherol in an oil-in-water emulsion is described in WO 95/17210.

Another enhanced adjuvant system involves the combination of a CpG-containing oligonucleotide and a saponin derivative as disclosed in WO 00/09159.

In certain preferred embodiments, the adjuvant used in the present invention is a glucopyranosyl lipid A (GLA) adjuvant, as described in pending U.S. Patent Application Publication No. 20080131466, the disclosure of which is incorporated herein by reference in its entirety.

Other illustrative adjuvants include Montanide ISA 720 (Seppic, France), SAF (Chiron, Calif., United States), ISCOMS (CSL), MF-59 (Chiron), the SBAS series of adjuvants (e.g., SBAS-2, AS2', AS2," SBAS-4, or SBAS6, available from SmithKline Beecham, Rixensart, Belgium), Detox, RC-529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties, and polyoxyethylene ether adjuvants, such as those described in WO 99/52549A1.

Compositions of the invention may also, or alternatively, comprise T cells specific for a Leishmania SMT antigen.

Such cells may generally be prepared in vitro or ex vivo, using standard procedures. For example, T cells may be isolated from bone marrow, peripheral blood, or a fraction of bone marrow or peripheral blood of a patient. Alternatively, T cells may be derived from related or unrelated humans, non-human mammals, cell lines or cultures.

T cells may be stimulated with a polypeptide of the invention, polynucleotide encoding such a polypeptide, and/or an antigen presenting cell (APC) that expresses such a polypeptide. Such stimulation is performed under conditions and for a time sufficient to permit the generation of T cells that are specific for the polypeptide. Preferably, the polypeptide or polynucleotide is present within a delivery vehicle, such as a microsphere, to facilitate the generation of specific T cells.

T cells are considered to be specific for a polypeptide of the invention if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., (1994) Cancer Res. 54:1065-1070). Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a polypeptide of the invention (100 ng/ml-100 n/ml, preferably 200 ng/ml-25 n/ml) for 3-7 days should result in at least a two fold increase in proliferation of the T cells. Contact as described above for 2-3 hours should result in activation of the T cells, as measured using standard cytokine assays in which a two fold increase in the level of cytokine release (e.g., TNF or IFN-γ) is indicative of T cell activation (see Coligan et al., (1998) Current Protocols in Immunology, vol. 1). T cells that have been activated in response to a polypeptide, polynucleotide or polypeptide-expressing APC may be CD4+ and/or CD8+. Protein-specific T cells may be expanded using standard techniques. Within preferred embodiments, the T cells are derived from a patient, a related donor or an unrelated donor, and are administered to the patient following stimulation and expansion.

In the compositions of the invention, formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

In certain applications, the compositions disclosed herein may be delivered via oral administration to a subject. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain circumstances it will be desirable to deliver the compositions disclosed herein parenterally, intravenously, intramuscularly, or even intraperitoneally as described, for example, in U.S. Pat. No. 5,543,158; U.S. Pat. No. 5,641,515 and U.S. Pat. No. 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., Remington's Pharmaceutical Sciences, 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions are prepared by incorporating the active compounds in the required amount in the appropriate solvent with the various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

In certain embodiments, the compositions may be delivered by intranasal sprays, inhalation, and/or other aerosol delivery vehicles. Methods for delivering genes, polynucleotides, and peptide compositions directly to the lungs via nasal aerosol sprays has been described e.g., in U.S. Pat. No. 5,756,353 and U.S. Pat. No. 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

In certain embodiments, the delivery may occur by use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

A pharmaceutical or immunogenic composition may, alternatively, contain an immunostimulant and a DNA molecule encoding one or more of the polypeptides or fusion proteins described above, such that a desired polypeptide is generated in situ. In such compositions, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a particular embodiment, the DNA may be introduced using a viral expression system (e.g., vaccinia or other pox virus, retrovirus, or adenovirus), which may involve the use of a non-pathogenic (defective), replication competent virus. Techniques for incorporating DNA into such expression systems are well known to those of ordinary skill in the art. The DNA may also be "naked," as described, for example, in Ulmer et al., (1993) *Science* 259:1745-1749 and reviewed by Cohen, (1993) *Science* 259:1691-1692. The uptake of naked DNA may be increased by coating the DNA onto biodegradable beads, which are efficiently transported into the cells.

The pharmaceutical compositions and vaccines of the invention may be used, for example, to induce protective immunity against *Leishmania* in a patient, such as a human or a dog, to prevent leishmaniasis or diminish its severity. The compositions and vaccines may also be used to stimulate an immune response, which may be cellular and/or humoral, in a patient, for treating an individual already infected. In one embodiment, for *Leishmania*-infected patients, the immune responses generated include a preferential Th1 immune response (i.e., a response characterized by the production of the cytokines interleukin-1, interleukin-2, interleukin-12 and/or interferon-$\gamma$, as well as tumor necrosis factor-$\alpha$). In another embodiment, for uninfected patients, the immune response involves production of interleukin-12 and/or interleukin-2, or the stimulation of gamma delta T-cells. In either category of patient, the response stimulated may include IL-12 production. Such responses may also be elicited in biological samples of PBMC or components thereof derived from *Leishmania*-infected or uninfected individuals. As noted above, assays for any of the above cytokines, as well as other known cytokines, may generally be performed using methods known to those of ordinary skill in the art, such as an enzyme-linked immunosorbent assay (ELISA).

Appropriate doses and methods of administration for these purposes can be readily determined by a skilled artisan using available knowledge in the art and/or routine techniques. Routes and frequency of administration, as well as dosage, for the above aspects of the present invention will vary from individual to individual and may parallel those currently being used in immunization against other infections, including protozoan, viral and bacterial infections. For example, in one embodiment, between 1 and 12 doses are administered over a 1 year period. Booster vaccinations may be given periodically thereafter as needed or desired. Of course, alternate protocols may be appropriate for individual patients. In a particular embodiment, a suitable dose is an amount of polypeptide or DNA that, when administered as described above, is capable of eliciting an immune response in an immunized patient sufficient to protect the patient from leishmaniasis for at least 1-2 years. In general, the amount of polypeptide present in a dose (or produced in situ by the DNA in a dose) ranges from about 100 ng to about 1 mg per kg of host, typically from about 10 µg to about 100 µg. Suitable dose sizes will vary with the size of the patient, but will typically range from about 0.1 mL to about 5 mL.

The SMT compositions, fusion polypeptides and polynucleotides are also useful as diagnostic reagents for detecting and/or monitoring *Leishmania* infection in a patient. For example, the compositions, fusion polypeptides, and polynucleotides of the invention may be used in in vitro and in vivo assays for detecting humoral antibodies or cell-mediated immunity against *Leishmania* for diagnosis of infection, monitoring of disease progression or test-of-cure evaluation.

The diagnostic methods and kits preferably employ an SMT polypeptide, portion, variant or the like, optionally in combination with one or more other *Leishmania* antigens. In certain embodiments, it will be preferred to use a multiple antigens as described herein, e.g., three or more, four or more, five or more, six or more, etc., in a diagnostic method of the invention. The antigens may be used in essentially any assay format desired, e.g., as individual antigens assayed separately, as multiple antigens assayed simultaneously, as antigens immobilized on a solid support such as an array, or the like.

In one embodiment, there are provided diagnostic kits for detecting *Leishmania* infection in a biological sample, comprising (a) a polypeptide comprising at least an immunogenic portion of an SMT polypeptide described herein, and (b) a detection reagent.

In another embodiment, there are provided diagnostic kits for detecting

*Leishmania* infection in a biological sample, comprising (a) an antibody or antigen binding fragment thereof that is specific for a polypeptide comprising at least an immunogenic portion of an SMT polypeptide described herein, and (b) a detection reagent.

In another embodiment, methods are provided for detecting the presence of *Leishmania* infection in a biological sample, comprising (a) contacting a biological sample with a monoclonal antibody that binds to an SMT polypeptide described herein; and (b) detecting in the biological sample the presence of *Leishmania* proteins that bind to the monoclonal antibody.

There are a variety of assay formats known to those of ordinary skill in the art for using purified antigen or fusion polypeptide to detect antibodies in a sample. See, e.g., Harlow and Lane, *Antibodies: A Laboratory Manual*, Cold Spring Harbor Laboratory, 1988. In one embodiment, the assay involves the use of polypeptide immobilized on a solid support to bind to and remove the antibody from the sample. The bound antibody may then be detected using a detection reagent that binds to the antibody/peptide complex and contains a detectable reporter group. Suitable detection reagents include antibodies that bind to the antibody/polypeptide complex and free polypeptide labeled with a reporter group (e.g., in a semi-competitive assay). Alternatively, a competitive assay may be utilized, in which an antibody that binds to the polypeptide is labeled with a reporter group and allowed to bind to the immobilized antigen after incubation of the antigen with the sample. The extent to which components of the sample inhibit the binding of the labeled antibody to the polypeptide is indicative of the reactivity of the sample with the immobilized polypeptide.

The solid support may be any solid material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptide may be bound to the solid support using any of a variety of techniques known and available in the art. The term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time.

In certain embodiments, the diagnostic assay employed is an enzyme linked immunosorbent assay (ELISA). This assay may be performed by first contacting a polypeptide antigen that has been immobilized on a solid support, commonly the well of a microtiter plate, with the sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

Once the polypeptide is immobilized on the support, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized polypeptide is then incubated with the sample, and antibody (if present in the sample) is allowed to bind to the antigen. The sample may be diluted with a suitable diluent, such as phosphate-buffered saline (PBS) prior to incubation. In general, an appropriate contact time (i.e., incubation time) is that period of time that is sufficient to detect the presence of antibody to *Leishmania* within an infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. Detection reagent may then be added to the solid support. An appropriate detection reagent is any compound that binds to the immobilized antibody-polypeptide complex and that can be detected by any of a variety of means known to those in the art. The detection reagent generally contains a binding agent (such as, for example, Protein A, Protein G, immunoglobulin, lectin or free antigen) conjugated to a reporter group. Illustrative reporter groups include enzymes (such as horseradish peroxidase), substrates, cofactors, inhibitors, dyes, radionuclides, luminescent groups, fluorescent groups and biotin. The conjugation of binding agent to reporter group may be achieved using standard methods known to those of ordinary skill in the art.

The detection reagent is then incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of *Leishmania* antibodies in a sample, the signal detected from the reporter group that remains bound to the solid support is generally compared to a signal that corresponds to a predetermined cut-off value. This cut-off value is preferably the average mean signal obtained when the immobilized antigen is incubated with samples from an uninfected patient. In general, a sample generating a signal that is three standard deviations above the mean is considered positive for *Leishmania* antibodies and *Leishmania* infection. In another embodiment, the cut-off value is determined using a Receiver Operator Curve, according to the method of Sackett et al., *Clinical Epidemiology: A Basic Science for Clinical Medicine*, p. 106-7 (Little Brown and Co., 1985). Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for *Leishmania* infection.

In another embodiment, a diagnostic assay may be performed in a flow-through or strip test format, wherein the antigen or fusion polypeptide is immobilized on a membrane such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of *Leishmania* antibodies in the sample. Such tests can typically be performed with a very small amount (e.g., one drop) of patient serum or blood.

In yet another embodiment, methods are provided for detecting *Leishmania* in a biological sample using antibodies (which may be polyclonal or monoclonal) and/or T-cells specific for one or more antigens, fusion polypeptides and/or immunogenic portions of the invention.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Protective Immunization Against Visceral Leishmaniasis Using Leishmania Sterol 24-c-Methyltransferase Formulated in Adjuvant A. Materials and Methods 1. Animals and Parasites Female C57BL/6 mice were purchased from Charles River Laboratories (Wilmington, Mass.), and were maintained in specific-pathogen-free conditions. Eight to twelve-week-old mice at the beginning of experiments were used. Promastigotes of *L. infantum* (MHOM/BR/82/BA-2) were cultured in MEM (Invitrogen, Carlsbad, Calif.) supplemented with 0.5× MEM essential amino acids solution (Invitrogen), 0.1 mM MEM non-essential amino acids (Invitrogen), 1 mM sodium pyruvate, 25 mM HEPES, 8.3 mM glucose, 26 mM sodium bicarbonate, 1 µg/ml para amino benzoic acid, 50 µg/ml gentamicin 10% heat-inactivated fetal bovine serum and 6 µg/ml hemin. Promastigotes of *L. donovani* and *L. major* (MHOM/IL/80/Friedlin) were kindly provided from Dr. David Sacks, National Institutes of Health, and cultured in Medium 199 as previously described (Belkaid et al., (2002) *J Immunol* 168: 3992-4000). Promastigotes in a late log or stationary phase were used for infections or antigen preparations.

2. Cloning of *L. infantum* SMT and Production of the Recombinant Protein

An open reading frame of *L. infantum* SMT was amplified by PCR using *L. infantum* genomic DNA with a set of primers, 5' CAA TTA CAT ATG TCC GCC GGT GGC CGT G (SEQ ID NO: 9), 3' CAA TTA AAG CTT CTA AGC CTG CTT GGA CGG (SEQ ID NO: 10). The amplified PCR product was inserted in-frame with a 6×His tag into the vector pET-28a (EMD Biosciences, San Diego, Calif.) and the insert was sequenced. The deduced amino acid sequence of *L. infantum* SMT was compared with those of SMTs from *L. donovani* (Accession No. AAR92098), *L. major* (CAJ09196), *Trypanosoma cruzi* (EAN81270) and *Candida albicans* (AAC26626), which were obtained from the NCBI database (www dot ncbi dot nlm dot nih dot gov), using the MegAlign software package (DNASTAR Inc., Madison, Wis.) by the Clustal method.

The pET-28a vector cloned for *L. infantum* SMT was transformed into *E. coli* Rosetta. Expression of the recombinant protein was induced by cultivation with 1M isopropyl-β-D-thiogalactoside. rSMT was then purified as 6×His-tagged proteins using Ni-NTA agarose (Qiagen Inc., Valencia, Calif.). Concentration of the purified protein was measured by BCA protein assay (Pierce Biotechnology Inc., Rockford, Ill.). Purity of the proteins was assessed by Coomassie blue-staining following SDS-PAGE. An endotoxin level of the protein was measured by a *Limulus amebocyte* lysate test (Cambrex Corporation, East Rutherford, N.J.) and shown to be below 10 EU/mg of protein.

3. Immunization of Mice

Mice were immunized with 10 µg of rSMT plus 20 µg of MPL®-SE adjuvant (GlaxoSmithKline Biologicals, Rixensant, Belgium) in a volume of 0.1 ml. Another group of mice was administrated with 10 µg of rSMT alone. Control groups received either saline or MPL®-SE adjuvant alone. The mice were immunized subcutaneously three times at three weeks intervals in the right hind footpad and at the base of the tail.

4. Western Blotting

Samples for immunoblotting were prepared by suspending promastigotes in SDS sample buffer followed by boiling for 5 min. Samples containing 5×10⁵ promastigotes were separated by SDS-PAGE and blotted on polyvinylidene difluoride membranes. Polyclonal Ab obtained from mice immunized with rSMT plus MPL®-SE adjuvant was used for western blotting. Sera from naïve mice were used at the same dilution as a control. The membranes were then probed with HRP-conjugated goat anti-mouse IgG. (Rockland Immunochemicals, Inc., Gilbertsville, Pa.). Development was performed using Chemiluminescent Super Sensitive HRP Substrate Kit (BioFX Laboratories, Owings Mills, Md.).

5. ELISA for Human Anti-SMT IgG rSMT was diluted in ELISA coating buffer, and 96-well plates were coated with 200 ng/well of antigen followed by blocking with phosphate-buffered saline containing 0.05% Tween-20 and 1% bovine serum albumin. Next, the plates were incubated with Brazilian VL patient sera (n=21) as well as sera from Chagas disease patients (n=10), endemic healthy donors (n=10) and non-endemic healthy donors (n=6) at 1:200 dilution. For total IgG, HRP-conjugated anti-human IgG (Rockland Immunochemicals) was used as the secondary Ab. For IgG subclass assay, HRP-conjugated anti-human IgG1, IgG2, IgG3 or IgG4 (Invitrogen) were used. The plates were developed with tetramethylbenzidine peroxidase substrate (Kirkegaard & Perry Laboratories, Gaithersburg, Md.) and read by a microplate reader at 450 nm (570 nm reference).

6. ELISA for Mouse Anti-SMT IgG

The ELISA protocol was similar to that described above but different primary and secondary antibodies were used. Three mice per group were bled one week after the last immunization for Ab ELISA. Mouse serum samples were diluted to 1:100 and applied to the plates in fivefold serial dilutions. Then the plates were incubated with HRP-conjugated goat anti-mouse IgG1 or IgG2a (Southern Biotech, Birmingham, Ala.). The plates were developed with the substrate and read by a microplate reader at a 450 nm wavelength. Endpoint titers were calculated with the GraphPad Prism software using an OD value of 0.1 as a cutoff.

7. Cytokine Assay Using Spleen Cells

Spleens were collected from three mice per group two weeks after the last immunization. 2×10⁵ splenocytes in complete RPMI medium (RPMI supplemented with 10% heat-inactivated fetal bovine serum, 100 U/ml of penicillin and 100 μg/ml of streptomycin) per well were plated in a 96-well plate and then stimulated with 3 μg/ml of con A, 100 μg/ml of *L. infantum* soluble lysate antigen (LiSLA), 10 μg/ml of rSMT or medium alone. Culture supernatants were collected after 72 hrs cultivation and tested the levels of IFN-γ and IL-10 by sandwich ELISA.

8. Intracellular Staining and Flow Cytometry

Spleens were collected from three mice per group two weeks after the last immunization. 1×10⁶ splenocytes in 100 μl of complete RPMI per well were plated in a round bottom 96-well plate and then stimulated with PMA/ionomycin, 10 μg/ml of rSMT or medium alone. Co-stimulation antibodies anti-CD28 (eBioscience, San Diego, Calif.) and anti-CD49d (eBioscience) were added to the media for a final concentration of 1 μg/ml in the well during stimulation. After 2 hours incubation at 37° C., brefeldin A (GolgiPlug: BD Biosciences, San Jose, Calif.) was added to the wells and the incubation resumed for an additional 12 hrs at 37° C. Cells were blocked with anti-CD16/32 (eBioscience) 1:50 in 50 ul and then stained with AlexaFluor 700-anti-CD3 (eBioscience), PerCP-anti-CD4 (BD Biosciences), PE-anti-CD8 (BD Biosciences). Then cells were fixed using the Cytofix/Cytoperm kit (BD Biosciences). Cells were again blocked with anti-CD16/32 and then intracellularly stained with FITC-anti-TNF-α (eBioscience), Pacific Blue-anti-IL-2 (eBioscience) and PE-Cy7-anti-IFN-γ (BD Biosciences). Cells were analyzed with a LSRII FACS machine (BD Biosciences) and the DIVA software.

9. Challenge of Mice with *L. infantum*

Seven mice per group were challenged with *L. infantum* three weeks after the last immunization. 5×10⁶ *L. infantum* promastigotes were suspended in Hank's balanced salt solution and injected i.v. into the tail vein of the mouse. At four weeks after the challenge, mice were sacrificed to collect spleens and livers to determine the numbers of parasites in these tissues by limiting dilution assay. The tissues were homogenated with glass grinders and the suspensions were twofold serially diluted with complete HOMEM in 96-well microplates with NNN blood agar. Each well was examined for the presence of parasites ten days after plating, and the numbers of parasites in the original tissues were calculated based on dilution factor of the last positive well.

B. Results

1. SMT is Expressed by *Leishmania* Species

Figure 3:
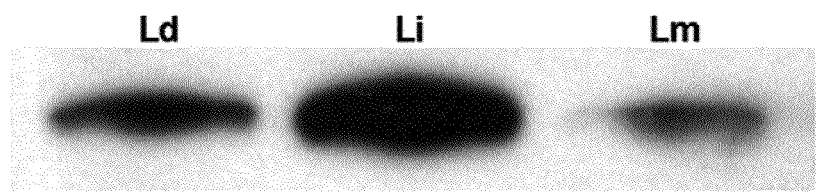
FIG. 3 shows expression of SMT by promastigotes of *L. donovani* (Ld), *L. infantum* (Li) and *L. major* (Lm).

An open reading frame of SMT was cloned from *L. infantum* total DNA by PCR amplification using specific primers. The size was 1,062 by and the sequence was 100% matched with the one on the database (LinJ36.4930; 1,062 bp, 353 amino acids, 39.8 kDa, obtained from GeneDB: www dot genedb dot org). A sequence analysis using the NCBI database (www dot ncbi dot nlm dot nih dot gov) revealed that *L. infantum* SMT has 99.6%, 96.6%, 81%, and 66.0% identity to SMTs from *L. donovani, L. major, L. braziliensis,* and *T. cruzi* respectively (FIG. 1).

rSMT was expressed in *E. coli* and purified (FIG. 2). An apparent molecular mass of the protein was as predicted (42 kDa). Mouse polyclonal Ab raised against rSMT was used for detection of native SMT in *Leishmania* species by western blot analysis. Anti-SMT Ab detected a band with apparent molecular sizes of 38 kDa, which is in a same range of the predicted size, in all the *Leishmania* species tested, i.e. *L. donovani*, L infantum and *L. major*, whereas the intensity of the bands was different (FIG. 3). Those bands were not detected when sera from naïve mice were used as the primary Ab.

2. VL Patient Sera Recognize rSMT

Figure 4:
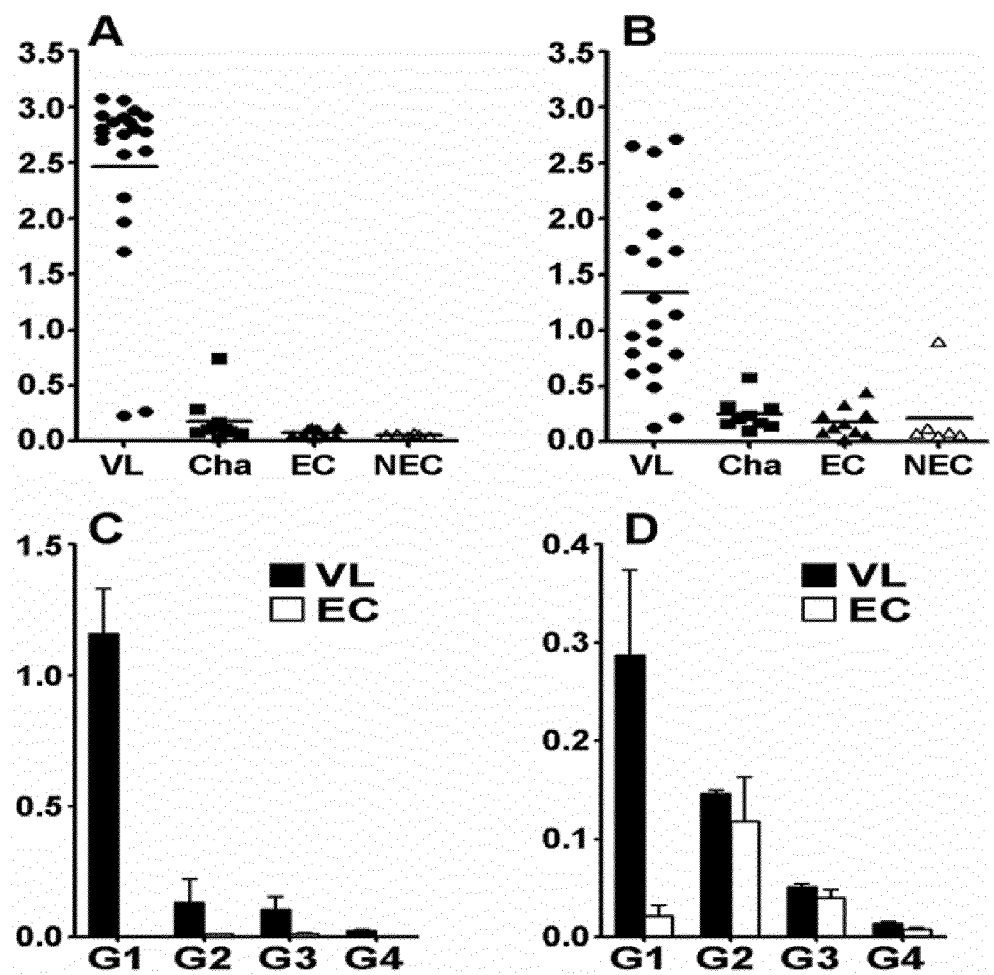
FIG. 4 shows the antibody responses of VL patients to SMT. (A and B) Sera from VL patients (n=21), Chagas patients (Cha: n=10), endemic healthy controls (EC: n=10) and non-endemic healthy donors (n=6) were tested for total IgG reactivity to rK39 (A) and rSMT (B) by ELISA and OD values of each individual are shown. Bars represent means of each group. (C and D) Shown are IgG subclass reactivity of VL patients (n=21) and endemic healthy controls (n=3) to rK39 (C) and rSMT (D). Means and SEM of each group are shown.

To determine antigenicity of *Leishmania* SMT in humans, examined the prevalence of antibodies to rSMT and rK39 in VL patients by ELISA using sera from 21 Brazilian VL patients. rK39 is a serodiagnostic antigen and the presence of antibodies to the antigen indicates active VL (Burns et al., (1993) *Proc Natl Acad Sci USA* 90:775779). 19 of the 21 showed strong Ab responses to rK39 and those responses were specific in VL patients (FIG. 4A). Those sera showed moderate to strong reactivity to rSMT, and these Ab responses seemed to be specific in VL patients, whereas one non-endemic healthy donor showed moderate response (FIG. 4B). rSMT was recognized by Sudanese VL patients infected with *L. donovani* (data not shown), suggesting that SMT is antigenic in both *L. donovani*- and *L. infantum*-infected patients.

The sera were further examined to determine their IgG subclasses. IgG1, IgG2 and IgG3 responses to rK39 were detected in VL patient sera and IgG1 was the predominant subclass (FIG. 4C). IgG1 response was predominant to rSMT as well, despite the titers were lower than those to rK39 (FIG. 4D). Some IgG2 responses were observed in VL patient sera to rSMT, but that was not VL-specific, as health donors showed IgG2 response to this antigen. Little IgG4 responses were detected to either rK39 or rSMT.

3. rSMT Plus MPL®-SE Adjuvant Induce Immune Responses with Th1 Characteristics

Figure 5:
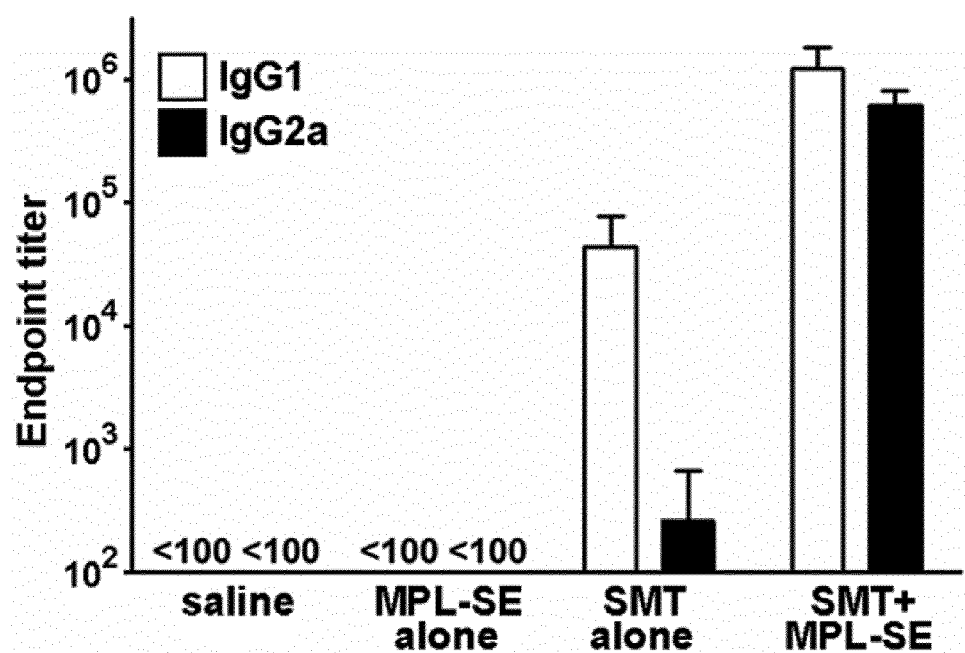
FIG. 5 shows the antibody responses of immunized mice to SMT. Levels of anti-SMT IgG1 and IgG2a of mice inoculated with saline, MPL®-SE adjuvant alone, rSMT alone or rSMT plus MPL®-SE adjuvant were evaluated by ELISA. Endpoint titers were calculated by using an OD value of 0.1 as a cutoff. Three mice were used per group and means and SEM of endpoint titers of each group are shown.

Since the rSMT plus MPL®-SE adjuvant vaccine induced protection against VL in mice, we then evaluated immune responses induced by the vaccine. Mice immunized with rSMT plus MPL®-SE adjuvant showed robust humoral responses to rSMT characterized by high levels of antigen-specific IgG1 and IgG2a (FIG. 5). In contrast, immunization with rSMT alone resulted in IgG1-dominant Ab responses. Mice injected with saline or adjuvant alone showed no Ab responses to rSMT.

Figure 6:
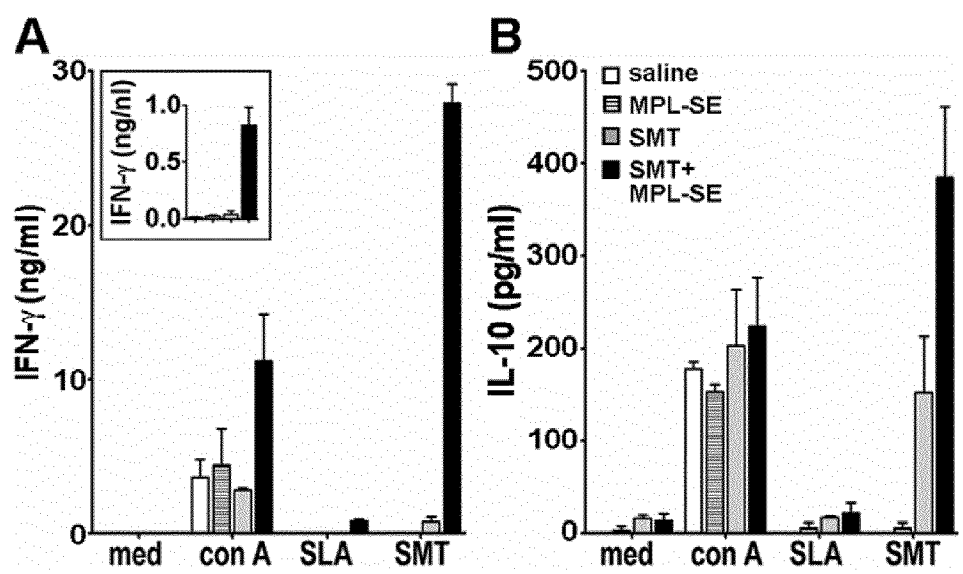
FIG. 6 shows cytokine production by immunized mice in stimulation with leishmanial antigens. Spleen cells from mice inoculated with saline alone, MPL®-SE adjuvant alone, SMT alone or SMT plus MPL®-SE adjuvant were stimulated in vitro with medium alone, con A, rSMT or SLA. Culture supernatants were collected after 72 hrs stimulation and the levels of IFN-γ (A) and IL-10 (B) in the supernatants were measured by sandwich ELISA. An inset shows IFN-γ responses in stimulation with SLA using a different scale. Mean and SEM of three mice in each group are shown.

To investigate cell-mediated responses brought about by the immunization, cytokine production by spleen cells in stimulation with rSMT or LiSLA were measured. Spleen cells from mice immunized with rSMT plus MPL®-SE adjuvant produced a high level of IFN-γ in response to rSMT (FIG. 6A). These mice also responded to LiSLA stimulation; albeit the magnitude of IFN-γ production was much lower than that observed with rSMT stimulation. In contrast, spleen cells from mice immunized with rSMT alone produced only a low level of IFN-γ in response to rSMT. Compared with administration of SMT alone, IFN-γ/IL-10 ratio was drastically improved when MPL®-SE adjuvant was co-injected with the antigen (FIG. 6B). No detectable cytokine production was found in saline or adjuvant alone groups in stimulation with rSMT or LiSLA.

Figure 7A:
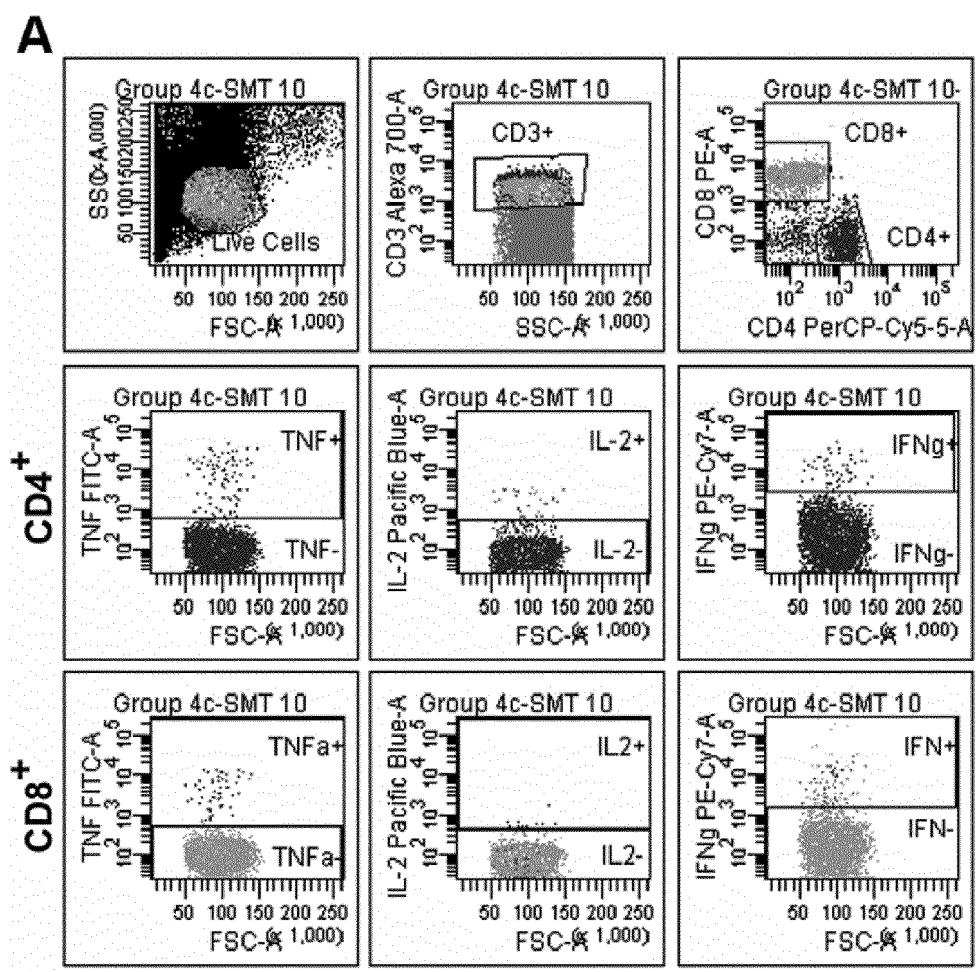
FIG. 7 shows the results of flow cytometric analysis of SMT-specific T-cells. (A) A representative of flow cytometry data. (B) TNF-α, IL-2 and IFN-γ production by CD4$^+$ and CD8$^+$ T-cells in response to SMT. Spleen cells from mice administrated with saline, MPL®-SE adjuvant alone, rSMT alone and rSMT plus MPL®-SE adjuvant were incubated with medium alone or in a presence of rSMT, and cytokine production was analyzed by flow cytometry. (C) Single-cell analysis of CD4$^+$ (left) and CD8$^+$ (right) T-cells producing multiple Th1-type cytokines

4. rSMT Plus MPL®-SE Adjuvant Induce Both CD4$^+$ and CD8$^+$ Cells Expressing Multiple Th1-Type Cytokines To further investigate cellular responses induced by rSMT plus MPL®-SE adjuvant vaccination, flow cytometric analysis of Th1-type cytokine production by CD4$^+$ and CD8$^+$ T-cells was performed. Spleen cells, which were harvested after in vitro cultivation with or without SMT, were gated based on forward and side scatter first, then CD3 expression (FIG. 7A). CD4$^+$ or CD8$^+$ cells were further gated from the CD3' population. Those populations were analyzed the frequency of cells producing TNF-α, IL-2 or IFN-γ.

Figure 7B:
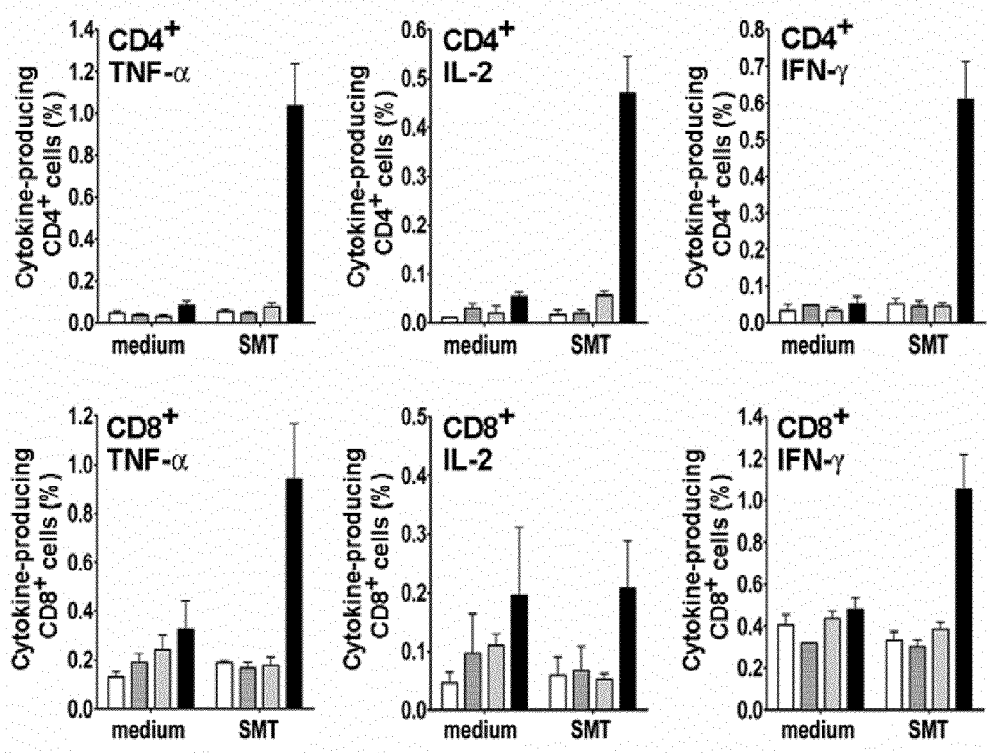

FACS data show that antigen-specific CD4$^+$ and CD8$^+$ cells were induced by rSMT plus MPL®-SE adjuvant vaccination (FIG. 7B). CD4$^+$ cells producing TNF-α, IL-2 or IFN-γ in stimulation with rSMT were found only in that group of mice. Antigen-specific CD8$^+$ cells were also found in mice administrated rSMT plus MPL®-SE adjuvant, and the frequency of those cells producing TNF-α or IFN-γ was high.

Figure 7C:
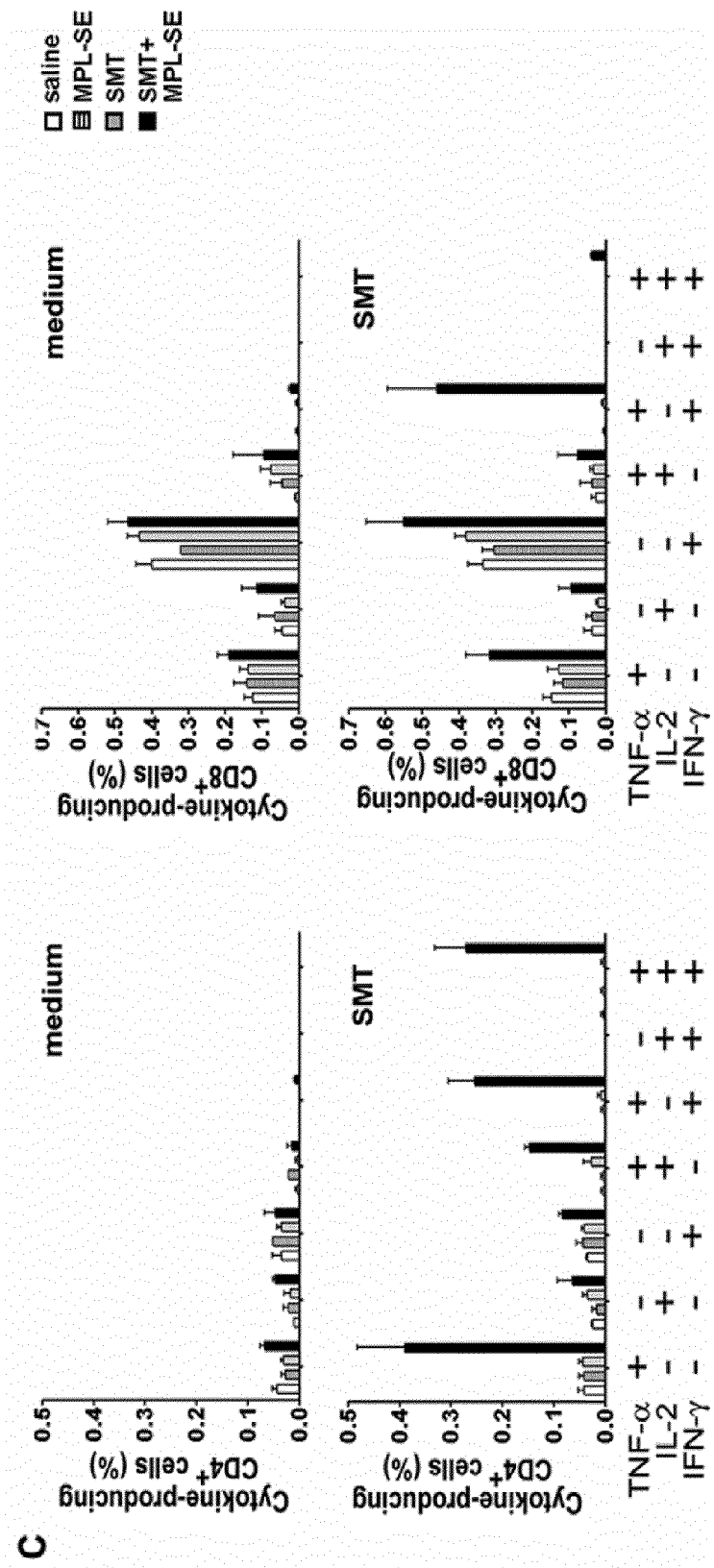

When CD4$^+$ and CD8$^+$ cells were further divided into seven distinct populations based on expression patterns of TNF-α, IL-2 or IFN-γ at a single-cell level, it was revealed that many of antigen-specific T-cells producing multiple cytokines were induced by rSMT plus MPL®-SE adjuvant (FIG. 7C). There were both CD4$^+$ and CD8$^+$ cells producing only TNF-α in stimulation with rSMT, whereas cells expressing only IFN-γ were little. Most of antigen-specific CD4$^+$ T-cells producing IFN-γ were co-expressing TNF-α or both TNF-α and IL-2. Also, many of the antigen-specific CD8$^+$ T-cells were producing both TNF-α and IFN-γ.

5. rSMT-Vaccinated Mice are Resistant Against L. infantum Infection

Figure 8:
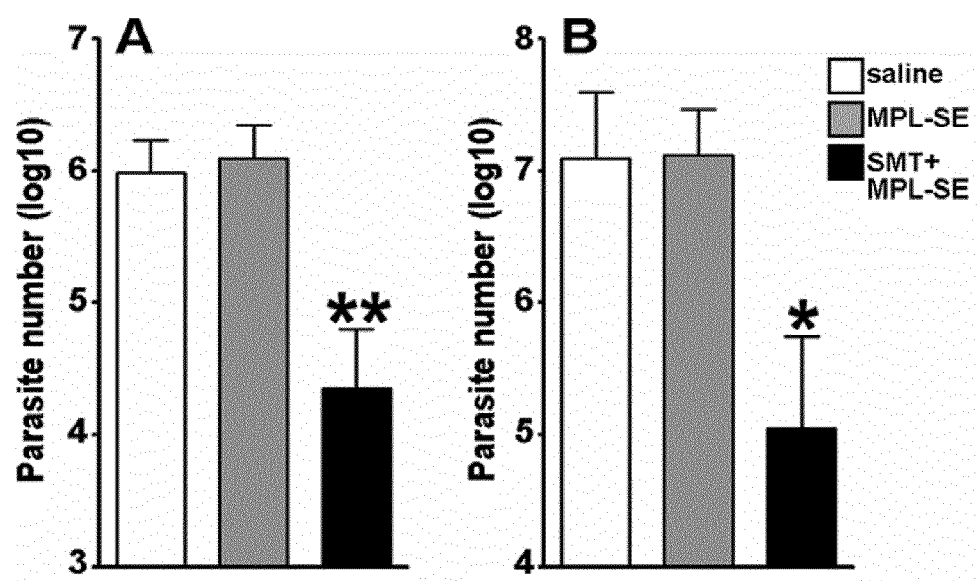
FIG. 8 shows the protection against *L. infantum* infection by SMT immunization. Mice inoculated with saline, MPL®-SE adjuvant or rSMT+MPL®-SE adjuvant were challenged with *L. infantum* and the numbers of parasites in spleens (A) and livers (B) were measured four weeks after the infection. Mean and SEM of five mice in each group are shown. *$P<0.05$ and **$P<0.01$ by unpaired t-test compared with both saline and MPL®-SE adjuvant groups. This is a representative of three independent experiments with similar results.

To evaluate the protective efficacy of rSMT plus MPL®-SE adjuvant vaccination against VL, immunized mice were challenged by intravenous injection of 5×10$^6$ L. infantum promastigotes. During L. infantum infection, C57BL/6 mice showed peak parasite burden in livers around four weeks of the infection (data not shown). Thus, we chose four weeks as a time point for determining parasite numbers in spleens and livers of challenged mice. Significant reduction of parasites was seen in mice immunized with rSMT plus MPL®-SE adjuvant compared with those in saline or adjuvant alone groups (FIG. 8). The immunized mice showed 43-fold and 55-fold reduction in the number of parasites in spleens, 111-fold and 117-fold reduction in livers compared with saline and adjuvant alone groups, respectively. There was no significant difference observed between saline and adjuvant alone groups. This protection in SMT-immunized mice was repeatedly observed with similar magnitude.

C. Discussion

Immunization with L. infantum SMT significantly protected mice from L. infantum, a causative agent of VL in humans and dogs, and this prophylactic effect was substantially better than with any previously reported vaccine candidate. There have been a limited number of vaccine candidates which have been shown to induce protection against VL in animal models (Basu et al., (2005) J Immunol 174:7160-7171; Ghosh et al., (2001) Vaccine 20:59-66; and Rafati et al., (2006) Vaccine 24:2169-2175). With most candidates, the levels of protection observed have been minimal, often only a two-fold reduction in parasite burdens. In mice, parasite numbers in liver show a peak around four weeks post infection and decline thereafter. In contrast, persistent infection of parasites is found in spleen. A higher degree of protection by SMT immunization was achieved by the present invention compared with previously reported antigens and the protection was seen in both spleen and liver.

Further, SMT is expressed by both L. infantum and L. donovani, the two causative agents of VL, as well as L. major, a causative agent of CL, and L. braziliensis, a causative agent of both CL and disseminated leishmaniasis (DL). This SMT expression pattern suggests that the antigen may also be useful in other forms of leishmaniasis. Furthermore, the lack of homology with mammalian proteins is expected to offer safety advantages when vaccinating with SMT. SMT is also found in other pathogens including parasites and fungi such as Trypanosoma spp. (Zhou et al., (2006) J Biol Chem 281: 6290-6296), Candida albicans (Jensen-Pergakes et al., (1998) Antimicrob Agents Chemother 42:1160-1167), and Pneumocystis carinii (Kaneshiro et al., (2001) J Eukaryot Microbiol Suppl:144S-146S). Thus, SMT also represents a vaccine candidate for treating conditions other than VL.

Example 2

Mice Immunized with rSMT are Protected from L. major Infection

BALB/c mice (Charles River Laboratories) were maintained in specific-pathogen-free conditions. Mice were eight to twelve weeks old at the beginning of experiments. Promastigotes of L. major (MHOM/IL/80/Friedlin) were grown at 25° C. in medium 199 supplemented with 20% heat-inactivated fetal bovine serum, 100 U of penicillin per ml, 100 μg of streptomycin per ml, 2 mM L-glutamine, 0.1 mM adenine, 40 mM HEPES, 0.25 mg of hemin per ml, and 0.31 mg of 6-biotin per ml. Promastigotes in a late log or stationary phase were used for infections or antigen preparations.

Groups of five mice were immunized. The first group was immunized with saline as a negative control. The second group was immunized with 10 μg of rSMT plus 20 μg of MPL®-SE adjuvant (GlaxoSmithKline Biologicals, Rixensant, Belgium) in a volume of 0.1 ml. As a challenge, 2,000 L. major promastigotes were suspended in 10 μl of phosphate buffered saline and injected intradermally into both the left and right ears. Mice were infected 3 weeks after completion of the immunization protocol.

Figure 9:
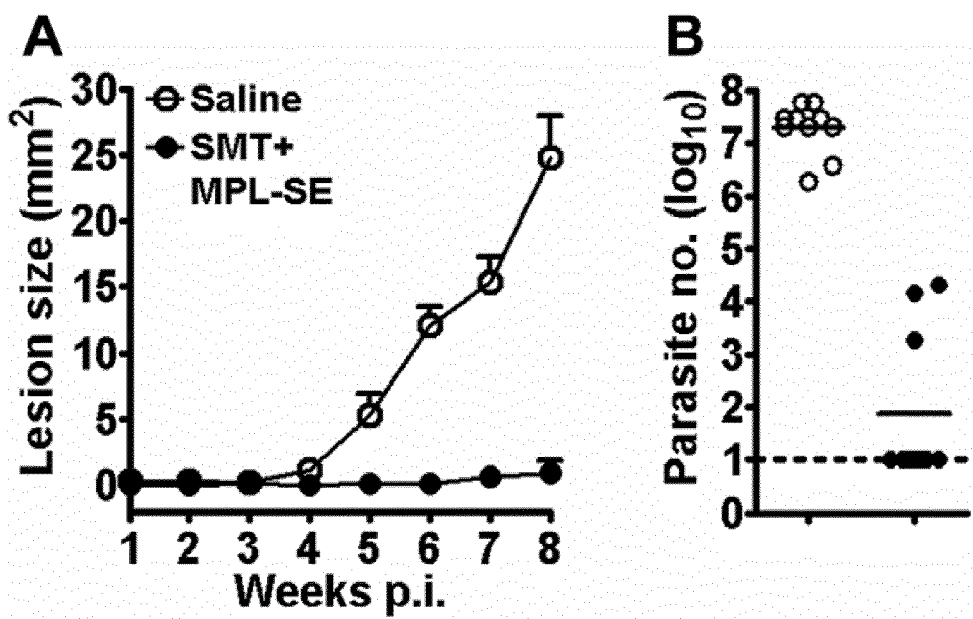
FIG. 9 shows the protection against *L. major* infection by SMT immunization. Mice inoculated with saline or rSMT+ MPL®-SE adjuvant were challenged with *L. major* in the ear. (A) Lesion development at the infection site was monitored for eight weeks. Mean and SEM of five mice in each group are shown. (B) At eight weeks post-infection, the numbers of parasites in the infected ears were evaluated by limiting dilution assay. Bars represent the mean values of individual groups. This experiment is representative of three independent experiments with similar results.

The progress of infection was monitored every week for eight weeks by measuring the diameter of the induration of the ear lesion with a metric caliper (FIG. 9A).

At eight weeks after the challenge, ear tissue was collected to determine the numbers of parasites by limiting dilution assay. The tissue was homogenated with grinders and the suspensions were twofold serially diluted with complete 199 medium in 96-well microplates with NNN blood agar. Each well was examined for the presence of parasites ten days after plating, and the numbers of parasites in the original tissues were calculated based on dilution factor of the last positive well (FIG. 9B).

The results of this experiment demonstrated that mice immunized with rSMT were significantly protected against *L. major*, a causative agent of cutaneous leishmaniasis. These results suggest that immunization with rSMT can be effective for protection against the various *Leishmania* pathogens that are the causative agents of visceral, cutaneous, mucosal, and disseminated leishmaniasis.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. A vaccine composition comprising a fusion polypeptide and an immunostimulant, wherein the fusion polypeptide comprises a first polypeptide and a second polypeptide, wherein the second polypeptide is heterologous fusion partner as to the first polypeptide, wherein the first polypeptide comprises a recombinant *Leishmania* sterol 24-c-methyltransferase (SMT) polypeptide comprising an amino acid sequence of SEQ ID NO:1, or a sequence having at least 95% identity to the amino acid sequence of SEQ ID NO:1, and the immunostimulant comprises a synthetic CpG unmethylated dinucleotide (CpG-containing oligonucleotide), a synthetic lipid A, monophosphoryl lipid (MPL) adjuvant, 3-de-O-acylated monophosphoryl lipid A (3D-MPL) adjuvant, an aminoalkyl glucosaminide 4-phosphates (AGP), a synthetic Toll-like receptor agonist or a combination thereof and the fusion polypeptide and the immunostimulant are present in amounts effective to induce an immune response.

2. A vaccine composition according to claim 1, wherein the immunostimulant is synthetic lipid A, MPL adjuvant, 3D-MPL adjuvant or a combination thereof.

3. A vaccine composition according to claim 1, wherein the immunostimulant is MPL adjuvant in a stable emulsion.

4. A method for inducing an immune response against leishmaniasis in a mammal comprising administering a vaccine composition according to claim 1.

* * * * *